United States Patent
Koehn et al.

(10) Patent No.: US 10,604,494 B2
(45) Date of Patent: Mar. 31, 2020

(54) ACYLATED N-(1,2,5-OXADIAZOL-3-YL)-, N-(1,3,4-OXADIAZOL-2-YL)-, N-(TETRAZOL-5-YL)- AND N-(TRIAZOL-5-YL)-ARYL CARBOXAMIDES, AND USE THEREOF AS HERBICIDES

(71) Applicant: Bayer CropScience Aktiengesellschaft, Monheim am Rhein (DE)

(72) Inventors: Arnim Koehn, Klein-Winternheim (DE); Ralf Braun, Ramberg (DE); Christian Waldraff, Bad Vilbel (DE); Hartmut Ahrens, Egelsbach (DE); Andreas Van Almsick, Karben (DE); Stefan Lehr, Liederbach (DE); Stephen David Lindell, Eppstein (DE); Hansjoerg Dietrich, Liederbach am Taunus (DE); Christopher Hugh Rosinger, Hofheim (DE); Elmar Gatzweiler, Bad Nauheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/763,385

(22) PCT Filed: Sep. 21, 2016

(86) PCT No.: PCT/EP2016/072345
§ 371 (c)(1),
(2) Date: Mar. 26, 2018

(87) PCT Pub. No.: WO2017/055146
PCT Pub. Date: Apr. 6, 2017

(65) Prior Publication Data
US 2018/0282290 A1 Oct. 4, 2018

(30) Foreign Application Priority Data
Sep. 28, 2015 (EP) .................................... 15187024

(51) Int. Cl.
| | |
|---|---|
| *C07D 257/06* | (2006.01) |
| *C07D 249/14* | (2006.01) |
| *C07D 271/08* | (2006.01) |
| *C07D 271/113* | (2006.01) |
| *C07D 403/12* | (2006.01) |
| *A01N 43/653* | (2006.01) |
| *A01N 43/713* | (2006.01) |
| *A01N 43/82* | (2006.01) |

(52) U.S. Cl.
CPC ......... *C07D 257/06* (2013.01); *A01N 43/653* (2013.01); *A01N 43/713* (2013.01); *A01N 43/82* (2013.01); *C07D 249/14* (2013.01); *C07D 271/08* (2013.01); *C07D 271/113* (2013.01); *C07D 403/12* (2013.01)

(58) Field of Classification Search
CPC .. C07D 249/14; C07D 257/06; C07D 271/08; C07D 271/113; C07D 403/12; A01N 43/653; A01N 43/713; A01N 43/82
See application file for complete search history.

(56) References Cited

U.S. PATENT DOCUMENTS

| | | |
|---|---|---|
| 8,288,316 B2 | 10/2012 | Koehn et al. |
| 8,481,749 B2 | 7/2013 | Braun et al. |
| 9,101,141 B2 | 8/2015 | Koehn et al. |
| 9,204,650 B2 | 12/2015 | Koehn et al. |
| 2012/0058892 A1 | 3/2012 | Braun et al. |
| 2014/0080705 A1 | 3/2014 | Koehn et al. |
| 2014/0371068 A1* | 12/2014 | Koehn ................. C07D 403/12 504/105 |

FOREIGN PATENT DOCUMENTS

| | | |
|---|---|---|
| WO | 2011035874 A1 | 3/2011 |
| WO | 2012/028579 A1 | 3/2012 |
| WO | 2012/126932 A1 | 9/2012 |

(Continued)

OTHER PUBLICATIONS

Aly, et al., "Synthesis and Reactions of Some Derivatives of 2-Amino-5 (4-PyridyI)-1,3,4- Oxadiazole," Egyptian Journal of Pharmaceutical Sciences, (1992), vol. 33, No. 3-4: 699-711.

(Continued)

*Primary Examiner* — John Pak
(74) *Attorney, Agent, or Firm* — McBee Moore & Vanik IP, LLC

(57) ABSTRACT

Acylated N-(1,2,5-oxadiazol-3-yl)-, N-(1,3,4-oxadiazol-2-yl)-, N-(tetrazol-5-yl)- and N-(triazol-5-yl)arylcarboxamides of the formula (I) and the use thereof as herbicides are described.

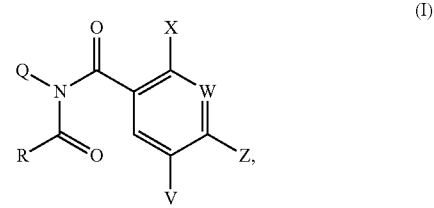

(I)

In this formula (I), R, V, X, Y and Z are radicals such as hydrogen, organic radicals such as alkyl, and other radicals such as halogen. Q is an oxadiazole, triazole or tetrazole radical. W is CY or N.

17 Claims, No Drawings

(56) References Cited

FOREIGN PATENT DOCUMENTS

WO 2013087577 A1 6/2013

OTHER PUBLICATIONS

Shchipanov, V.P., "The Tautomerism of 5-Aminotetrazole," Khimiya Geterotsiklicheskikh Soedinenii, (1969), vol. 5, No. 5: 923-6.
Gehlen, et al.;, "Bildung Von 2-Amino-5-Aminoalkyl-1.3.4-0xdiazolen Uno Deren Umwandlung in 1.2.4-Triazole Und Triazolone," Justus Liebigs Annalen der Chemie, (1962), vol. 651: 128-32.
PCT International Search Report for PCT/EP2016/072345, dated Oct. 24, 2016.

* cited by examiner

ACYLATED N-(1,2,5-OXADIAZOL-3-YL)-, N-(1,3,4-OXADIAZOL-2-YL)-, N-(TETRAZOL-5-YL)- AND N-(TRIAZOL-5-YL)-ARYL CARBOXAMIDES, AND USE THEREOF AS HERBICIDES

CROSS-REFERENCE TO RELATED APPLICATIONS

This application is a National Stage entry of International Application No. PCT/EP2016/072345, filed Sep. 21, 2016, which claims priority to European Patent Application No. 15187024.3, filed Sep. 28, 2015.

BACKGROUND

Field

The invention relates to the technical field of the herbicides, especially that of the herbicides for selective control of weeds and weed grasses in crops of useful plants.

Description of Related Art

WO 2011/035874 A1 describes N-(1,2,5-oxadiazol-3-yl) arylcarboxamides as herbicides. WO 2012/028579 A1 discloses herbicidally active N-(tetrazol-5-yl)- and N-(triazol-5-yl)arylcarboxamides. WO 2012/126932 A1 describes N-(1,3,4-oxadiazol-2-yl)arylcarboxamides as herbicides.

AL Y, A. S. ET AL: "Synthesis and reactions of some derivatives of 2-amino-5-(4-pyridyl)-1,3,4-oxadiazole", EGYPTIAN JOURNAL OF PHARMACEUTICAL SCIENCES, 33(3-4), 699-711, 1992, discloses the compound N-benzoyl-N-[5-(pyridin-4-yl)-1,3,4-oxadiazol-2-yl]benzamide.

SHCHIPANOV, V. P.: "Tautomerism of 5-aminotetrazole. VII. Synthesis, structure, and spectra of diacyl derivatives of 1- and 2-methyl-5-aminotetrazoles", KHIMIYA GETEROTSIKLICHESKIKH SOEDINENII, (5), 923-926, 1969, discloses the compounds N-acetyl-N-(1-methyltetrazol-5-yl)benzamide and N-benzoyl-N-(1-methyltetrazol-5-yl)benzamide.

GEHLEN, HEINZ ET AL: "2-Amino-1,3,4-oxadiazoles. VIII. Formation of 2-amino-5-aminoalkyl-1,3,4-oxadiazoles and their conversion into 1,2,4-triazoles and triazolones", JUSTUS LIEBIGS ANNALEN DER CHEMIE, 651, 128-132, 1962, discloses the compound N-benzoyl-N-{5-[4-({[-(methylsulfonyl)phenyl]amino}methyl)phenyl]-1,3,4-oxadiazol-2-yl}benzamide.

There is no description of any herbicidal effect of the compounds disclosed in the three aforementioned documents.

SUMMARY

It was an object of the present invention to provide further herbicidally active compounds.

It has now been found that benzoylamides substituted by particular radicals on the nitrogen atom are of particularly good suitability as herbicides.

The present invention thus provides N-(1,2,5-oxadiazol-3-yl)-, N-(1,3,4-oxadiazol-2-yl)-, N-(tetrazol-5-yl)- and N-(triazol-5-yl)arylcarboxamides or salts thereof of the formula (I)

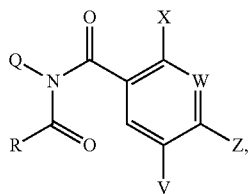

in which the symbols and indices are defined as follows:
R is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkyl-$(C_1-C_6)$-alkyl, $(C_3-C_6)$-halocycloalkyl-$(C_1-C_6)$-alkyl, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-C(O)$R^1$, $(C_1-C_6)$-alkyl-CN, $(C_1-C_6)$-alkyl-$SO_2OR^1$, $(C_1-C_6)$-alkyl-CON$(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $COOR^1$, $CON(R^1)_2$, or phenyl, heteroaryl, heterocyclyl or benzyl, each substituted by s radicals from the group consisting of X, Y, Z and V, W is N or CY, X and Z are each independently hydrogen, nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$SO_2OR^1$, $(C_1-C_6)$-alkyl-CON$(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, or heteroaryl, heterocyclyl or phenyl, each substituted by s radicals from the group of methyl, ethyl, methoxy, nitro, trifluoromethyl and halogen, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, COW, $COOR^1$, $OCOOR^1$, $NR^1COOR^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-CON$(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $CH=NOR^1$, $(C_1-C_6)$-alkyl-CH=NOR$^1$, $(C_1-C_6)$-alkyl-O—N=C($R^1$)$_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, or Y and Z together with the two atoms to which they are bonded form a 5-, 6- or 7-membered, unsaturated, partly saturated or saturated ring which, as well as carbon atoms, in each case comprises s nitrogen atoms, n oxygen atoms, n sulfur atoms and n S(O), S(O)$_2$, C=N—R$^{17}$, C(OR$^{17}$)$_2$, C[—O—(CH$_2$)$_2$—O—] or C(O) elements as ring members, wherein the carbon atoms are substituted by s radicals from the group consisting of halogen, cyano, (C$_1$-C$_6$)-alkyl, (C$_2$-C$_{10}$)-alkenyl, (C$_2$-C$_{10}$)-alkynyl, (C$_1$-C$_6$)-haloalkyl, (C$_1$-C$_6$)-alkoxy, phenoxy, halo-(C$_1$-C$_6$)-alkoxy, (C$_3$-C$_8$)-cycloalkyl, (C$_2$-C$_8$)-alkoxyalkyl and phenyl, wherein the nitrogen atoms are substituted by n radicals from the group consisting of (C$_1$-C$_6$)-alkyl and phenyl, and in which the aforementioned phenyl radicals are substituted by s radicals from the group consisting of cyano, nitro, halogen, (C$_1$-C$_6$)-alkyl, (C$_1$-C$_6$)-haloalkyl and (C$_1$-C$_6$)-alkoxy, V is hydrogen, nitro, halogen, cyano, (C$_1$-C$_4$)-alkyl, (C$_1$-C$_4$)-haloalkyl, OR$^1$, S(O)$_n$R$^2$, R$^1$ is hydrogen, (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^2$ is (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl, (C$_1$-C$_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^3$ is hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ is (C$_1$-C$_6$)-alkyl, (C$_2$-C$_6$)-alkenyl or (C$_2$-C$_6$)-alkynyl, (C$_3$-C$_6$)-cycloalkyl or (C$_3$-C$_6$)-cycloalkyl-(C$_1$-C$_6$)-alkyl, R$^5$ is (C$_1$-C$_4$)-alkyl, n is 0, 1 or 2, s is 0, 1, 2 or 3, Q is a Q1, Q2, Q3 or Q4 radical

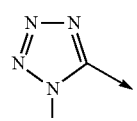

(Q1)

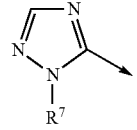

(Q2)

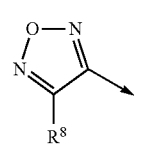

(Q3)

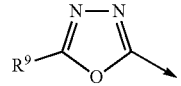

(Q4)

R$^6$ and R$^7$ are independently (C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, where these 6 aforementioned radicals are each substituted by s radicals from the group consisting of nitro, cyano, SiR$^{12}$$_3$, PO(OR$^{12}$)$_3$, S(O)$_n$—(C$_1$-C$_6$)-alkyl, (C$_1$-C$_6$)-alkoxy, halo-(C$_1$-C$_6$)-alkoxy, N(R$^{10}$)$_2$, COR$^{10}$, COOR$^{10}$, OCOR$^{10}$, OCO$_2$R$^{10}$, NR$^{10}$COR$^{10}$, NR$^{10}$SO$_2$R$^{11}$, (C$_3$-C$_6$)-cycloalkyl, heteroaryl, heterocyclyl, phenyl, D-heteroaryl, D-heterocyclyl, D-phenyl or D-benzyl, and where the 7 latter radicals are substituted by s radicals from the group of methyl, ethyl, methoxy, trifluoromethyl and halogen, and where heterocyclyl bears n oxo groups, or R$^6$ and R$^7$ are each (C$_3$-C$_7$)-cycloalkyl, heteroaryl, heterocyclyl or phenyl, each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, R$^8$ is hydrogen, (C$_1$-C$_6$)-alkyl, (C$_3$-C$_7$)-cycloalkyl, halo-(C$_1$-C$_6$)-alkyl, (C$_1$-C$_6$)-alkoxy, halo-(C$_1$-C$_6$)-alkoxy, (C$_2$-C$_6$)-alkenyl, (C$_2$-C$_6$)-alkenyloxy, halo-(C$_2$-C$_6$)-alkenyl, (C$_2$-C$_6$)-alkynyl, (C$_2$-C$_6$)-alkynyloxy, halo-(C$_2$-C$_6$)-alkynyl, cyano, nitro, methylsulfenyl, methylsulfinyl, methylsulfonyl, (C$_1$-C$_6$)-alkylcarbonylamino, (C$_1$-C$_6$)-alkoxycarbonylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each substituted by s radicals from the group consisting of methyl, ethyl, methoxy, trifluoromethyl and halogen;

R$^9$ is hydrogen, (C$_1$-C$_6$)-alkyl, R$^{13}$O—(C$_1$-C$_6$)-alkyl, CH$_2$R$^{14}$, (C$_3$-C$_7$)-cycloalkyl, halo-(C$_2$-C$_6$)-alkenyl, halo-(C$_2$-C$_6$)-alkenyl, (C$_2$-C$_6$)-alkynyl, halo-(C$_2$-C$_6$)-alkynyl, OR$^{13}$, NHR$^{13}$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals from the group consisting of halogen, nitro, cyano, (C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, R$^{10}$ is hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl or phenyl, R$^{11}$ is (C$_1$-C$_6$)-alkyl, (C$_2$-C$_6$)-alkenyl, (C$_2$-C$_6$)-alkynyl or phenyl, R$^{12}$ is (C$_1$-C)-alkyl, R$^{13}$ is hydrogen, (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-

$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^{15}$-heteroaryl or ($C_1$-$C_6$)-alkyl-NR$^{15}$-heterocyclyl, where the 21 latter radicals are substituted by s radicals from the group consisting of cyano, halogen, nitro, thiocyanato, OR$^{15}$, S(O)$_n$R$^{16}$, N(R$^{15}$)$_2$, NR$^{15}$OR$^{15}$, COR$^{15}$, OCOR$^{15}$, SCOR$^{16}$, NR$^{15}$COR$^{15}$, NR$^{15}$SO$_2$R$^{16}$, CO$_2$R$^{15}$, COSR$^{16}$, CON(R$^{15}$)$_2$ and ($C_1$-$C_4$)-alkoxy-($C_2$-$C_6$)-alkoxycarbonyl, and where heterocyclyl bears n oxo groups, R$^{14}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, ($C_3$-$C_6$)-alkoxy, ($C_3$-$C_6$)-cycloalkyl, or heteroaryl, heterocyclyl or phenyl, each substituted by s radicals from the group consisting of methyl, ethyl, methoxy, trifluoromethyl and halogen;

R$^{15}$ is hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, R$^{16}$ is ($C_1$-$C_6$)-alkyl, ($C_2$-$C_6$)-alkenyl or ($C_2$-$C_6$)-alkynyl, R$^{17}$ is ($C_1$-$C_6$)-alkyl, halo-($C_1$-$C_6$)-alkyl, ($C_1$-$C_6$)-alkoxy and halo-($C_1$-$C_6$)-alkoxy, s is 0, 1, 2 or 3, n is 0, 1 or 2, D is O, S, or NR$^{11}$, with the proviso that V, W, X, Y and Z are not simultaneously hydrogen.

DETAILED DESCRIPTION OF A PREFERRED EMBODIMENT

Preference is given to compounds of the general formula (I) in which

R is hydrogen, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_3$-$C_6$)-haloalkynyl, ($C_3$-$C_6$)-cycloalkyl, ($C_3$-$C_6$)-cycloalkyl-($C_1$-$C_6$)-alkyl, ($C_3$-$C_6$)-halocycloalkyl-($C_1$-$C_6$)-alkyl, ($C_1$-$C_6$)-alkyl-S(O)$_n$R$^2$, ($C_1$-$C_6$)-alkyl-OR$^1$, ($C_1$-$C_6$)-alkyl-OCOR$^1$, ($C_1$-$C_6$)-alkyl-OSO$_2$R$^2$, ($C_1$-$C_6$)-alkyl-COOR$^1$, ($C_1$-$C_6$)-alkyl-C(O)R$^1$, ($C_1$-$C_6$)-alkyl-CN, ($C_1$-$C_6$)-alkyl-SO$_2$OR$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, COOR$^1$, CON(R$^1$)$_2$, or phenyl, heteroaryl, heterocyclyl or benzyl, each substituted by s radicals from the group consisting of X, Y, Z and V, W is N or CY, X and Z are each independently hydrogen, halogen, ($C_1$-$C_6$)-alkyl, ($C_1$-$C_6$)-haloalkyl, ($C_2$-$C_6$)-alkenyl, ($C_3$-$C_6$)-cycloalkyl, ($C_3$-$C_6$)-halocycloalkyl, OR$^1$, S(O)$_n$R$^2$, SO$_2$N(R$^1$)$_2$, NR$^1$SO$_2$R$^2$, NR$^1$COR$^1$, ($C_1$-$C_6$)-alkyl-S(O)$_n$R$^2$, ($C_1$-$C_6$)-alkyl-OR$^1$, or heteroaryl, heterocyclyl or phenyl, each substituted by s radicals from the group of methyl, ethyl, methoxy, nitro, trifluoromethyl and halogen, Y is hydrogen, ($C_2$-$C_6$)-alkenyl, COR$^1$, CO$_2$R$^1$, OCO$_2$R$^1$, NR$^1$CO$_2$R$^1$, C(O)N(R$^1$)$_2$, NR$^1$C(O)N(R$^1$)$_2$, OC(O)N(R$^1$)$_2$, C(O)N(R$^1$)OR$^1$, NR$^1$SO$_2$R$^2$, NR$^1$COR$^1$, OR$^1$, S(O)$_n$R$^2$, SO$_2$N(R$^1$)$_2$, ($C_1$-$C_6$)-alkyl-S(O)$_n$R$^2$, ($C_1$-$C_6$)-alkyl-OR$^1$, ($C_1$-$C_6$)-alkyl-OCOR$^1$, ($C_1$-$C_6$)-alkyl-CO$_2$R$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, N(R$^1$)$_2$, CH=NOR$^1$, ($C_1$-$C_6$)-alkyl-CH=NOR$^1$, ($C_1$-$C_6$)-alkylheteroaryl, ($C_1$-$C_6$)-alkylheterocyclyl, heteroaryl or heterocyclyl, where the 4 latter radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl bears n oxo groups, V is hydrogen, Cl, OMe, methyl or ethyl, R$^1$ is hydrogen, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and ($C_1$-$C_4$)-alkoxy-($C_2$-$C_6$)-alkoxycarbonyl, and where heterocyclyl bears n oxo groups, R$^2$ is ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O—($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl, ($C_1$-$C_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and ($C_1$-$C_4$)-alkoxy-($C_2$-$C_6$)-alkoxycarbonyl, and where heterocyclyl bears n oxo groups, R$^3$ is hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, R$^4$ is ($C_1$-$C_6$)-alkyl, ($C_2$-$C_6$)-alkenyl or ($C_2$-$C_6$)-alkynyl, ($C_3$-$C_6$)-cycloalkyl or ($C_3$-$C_6$)-cycloalkyl-($C_1$-$C_6$)-alkyl, n is 0, 1 or 2, s is 0, 1, 2 or 3, Q is a Q1, Q2, Q3 or Q4 radical

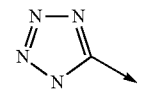 (Q1)

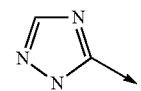 (Q2)

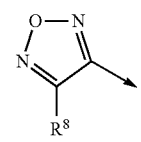 (Q3)

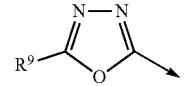 (Q4)

$R^6$ and $R^7$ are independently $(C_1\text{-}C_6)$-alkyl, halo-$(C_1\text{-}C_6)$-alkyl, $(C_2\text{-}C_6)$-alkenyl, where these 3 aforementioned radicals are each substituted by s $(C_1\text{-}C_6)$-alkoxy radicals, $R^8$ is chlorine, methyl, methoxymethyl, amino or acetylamino, $R^9$ is methyl, ethyl, methoxymethyl or methoxyethyl, with the proviso that V, W, X, Y and Z are not simultaneously hydrogen.

Particular preference is given to compounds of the general formula (I) in which R is methyl, or phenyl substituted in each case by s radicals from the group consisting of X, Y and Z, W is CY, X is F, $C_1$, Br, methyl, ethyl, cyclopropyl, trifluoromethyl, methoxy, methoxymethyl, methoxyethoxymethyl, SMe or $SO_2Me$, Z is hydrogen, F, $C_1$, Br, I, methyl, ethyl, trifluoromethyl, difluoromethyl, pentafluoroethyl, methylsulfonyl or ethylsulfonyl, Y is hydrogen, SMe, S(O)Me, $SO_2Me$, SEt, S(O)Et, $SO_2Et$, $CH_2OMe$, $CH_2OEt$, $CH_2OCH_2CF_3$, $CH_2SMe$, $CH_2S(O)Me$, $CH_2SO_2Me$, vinyl, C(O)Me, C(O)Et, C(O)cPr, $CO_2Me$, CHN=OMe, 4,5-dihydro-1,2-oxazol-3-yl, 5-methyl-4,5-dihydro-1,2-oxazol-3-yl, 5-methyl-4,5-dihydro-1,2-oxazol-3-yl, 5-cyanomethyl-4,5-dihydro-1,2-oxazol-3-yl, 4,5-dihydro-1,2-oxazol-5-yl, 3-methyl-4,5-dihydro-1,2-oxazol-5-yl, 1H-pyrazol-1-yl, 1H-1,2,3-triazol-1-yl, 2H-1,2,3-triazol-2-yl, 1H-1,2,4-triazol-1-yl, pyrolidin-2-on-1-yl, morpholin-3-on-4-yl, OMe, OEt, OnPr, $OCH_2cPr$, $OCH_2CH_2F$; $OCH_2CH_2OMe$ or $OCH_2CH_2CH_2OMe$, V is hydrogen, Q is a Q1, Q2, Q3 or Q4 radical

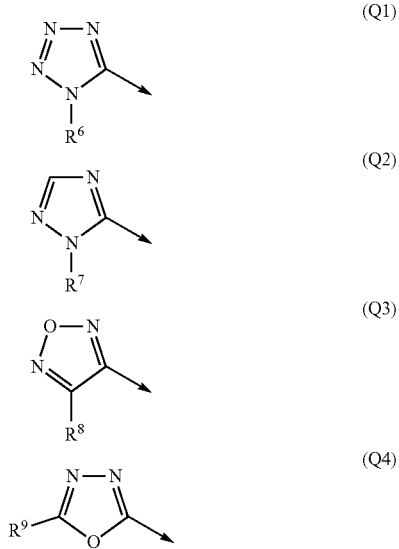

$R^6$ is methyl or ethyl,
$R^7$ is methyl,
$R^8$ is chlorine or methyl,
$R^9$ is methyl,
s is 0, 1, 2 or 3.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned. The same applies to the formation of ring systems by different atoms and elements. At the same time, the scope of the claims shall exclude those compounds known by the person skilled in the art to be chemically unstable under standard conditions.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically. Owing to the oxime ether structure, the compounds of the invention may also occur as geometric isomers (E/Z isomers). The invention also relates to all the E/Z isomers and mixtures thereof that are encompassed by the general formula (I) but are not defined specifically.

The compounds of the formula (I) are capable of forming salts. Salts can be formed by the action of a base on those compounds of the formula (I) which bear an acidic hydrogen atom, for example in the case that $R^1$ contains a COOH group or a sulfonamide group $—NHSO_2—$. Examples of suitable bases are organic amines such as trialkylamines, morpholine, piperidine or pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R''R''']⁺ in which R to R''' are each independently an organic radical, especially alkyl, aryl, aralkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugate base of the acid as the anion.

Inventive compounds can be prepared, for example, by the method specified in scheme 1, by reacting arylcarboxamide (II) with an acid chloride or an anhydride of the general formula (III):

Scheme 1

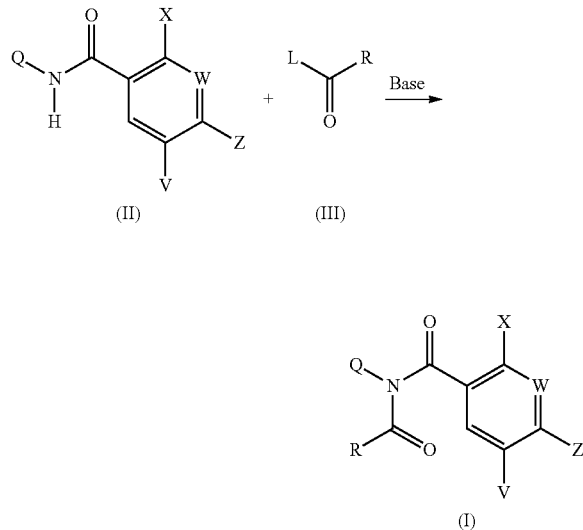

The arylcarboxamides of the formula (II) are known in principle and can be prepared, for example, by the methods described in WO2011/035874 A1, WO2012/123416 A1, WO 2012/028579 A1 and WO2012/126932.

Inventive compounds having two identical acyl radicals can also be prepared, for example, by the method specified in scheme 2, by reacting an amine of the formula (IV) with an acid chloride (V):

Scheme 2

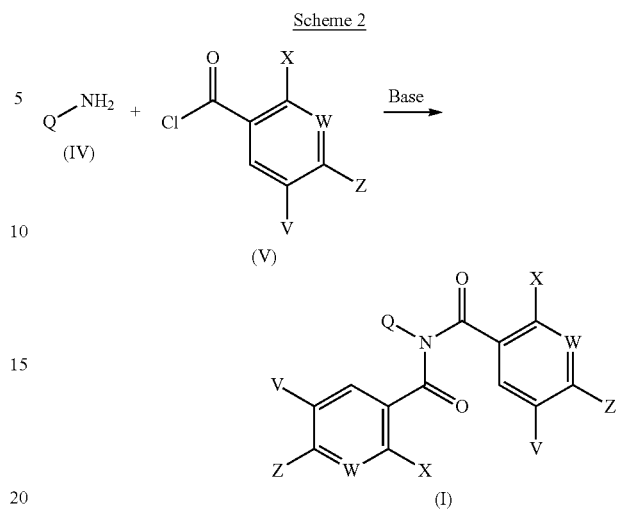

Inventive compounds having two identical acyl radicals can also be prepared by the method specified in scheme 3, by reacting an amine of the formula (IV) with an acid of the formula (VI):

Scheme 3

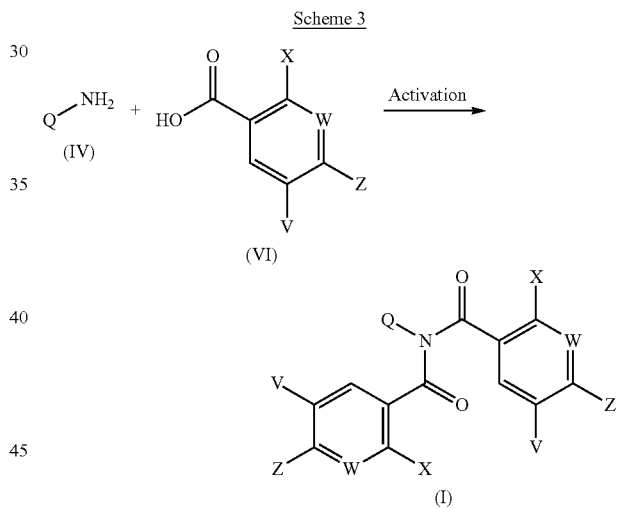

For the activation, it is possible to use dehydrating reagents which are typically for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P), etc.

The benzoyl chlorides of the formula (V) or their parent benzoic acids of the formula (VI) are known in principle and can be prepared, for example, by the methods described in U.S. Pat. No. 6,376,429 B1, EP 1 585 742 A1 and EP 1 202 978 A1.

Collections of compounds of the formula (I) which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MuItiPROBE Automated Workstations from Perkin Elmer, Waltham, Mass. 02451, USA. For the parallelized purification of compounds of the general formula (I) or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the general formula (I) can take place completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described herein gives compounds of the formula (I) in the form of substance collections, which are called libraries. The present invention also provides libraries comprising at least two compounds of the formula (I).

The inventive compounds of the formula (I), referred to hereinbelow as "compounds of the invention", have an excellent herbicidal effectiveness against a broad spectrum of economically important mono- and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material.

It is preferable, with respect to transgenic crops, to use the compounds of the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other types of vegetable. Preferably, the compounds of the invention can be used as herbicides in crops of useful plants which are resistant, or have been made resistant by genetic engineering, to the phytotoxic effects of the herbicides.

It is preferred to use the compounds of the invention in economically important transgenic crops of useful plants and ornamentals, for example of cereals such as wheat, barley, rye, oats, millet/sorghum, rice, cassava and corn or else crops of sugar beet, cotton, soybean, oilseed rape, potato, tomato, peas and other types other vegetable. Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659), transgenic crop plants, for example cotton, capable of producing *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature, for example, the abovementioned novel properties ("gene stacking") through combinations.

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition Cold Spring Harbor Laboratory Press, Cold Spring Harbor, N.Y., or Winnacker "Gene and Klone [Genes and clones]", VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227, Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th Ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers).

Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E.

Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10 to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

The examples which follow illustrate the invention.

A. Chemical Examples

1. Synthesis of 2-(methylsulfonyl)-4-trifluoromethyl-N-acetyl-N-(1-methyltetrazol-5-yl)benzamide (Table Example No. 13-1)

To 175 mg (0.5 mmol) of 2-(methylsulfonyl)-4-trifluoromethyl-N-(1-methyltetrazol-5-yl)benzamide in 5 ml of THF under argon at 0° C. are added 14 mg (0.55 mmol) of sodium hydride (95%). After stirring for 10 min, 47 mg (0.6 mmol) of acetyl chloride are added. The mixture is stirred at 0° C. for 1 h and then quenched with 2 mL of saturated sodium bicarbonate solution. The mixture is diluted with ethyl acetate and water, and the organic phase is washed with saturated sodium bicarbonate solution and sodium chloride solution, dried over Na2SO4 and concentrated. Yield 143 mg (73%).

2. Synthesis of 3-(ethoxycarbonyl)-2-methyl-4-(methylsulfanyl)-N-(3-(ethoxycarbonyl)-2-methyl-4-(methylsulfanyl)benzoyl)-N-(1-methyltetrazol-5-yl) benzamide (Table Example No. 1-453)

To 525 mg (2.06 mmol) of 3-(ethoxycarbonyl)-2-methyl-4-(methylsulfanyl)benzoic acid, 313 mg (3.09 mmol) of 1-methyl-5-aminotetrazole in 3 ml of pyridine are added, while cooling with an ice bath, 367 mg (3.09 mmol) of thionyl chloride. The mixture is stirred at RT for 3 days, then 0.2 mL of water is added, the mixture is stirred at RT for 30 min, and EA and 2 N HCl are added. The organic phase removed is washed once again with 2 N HCl and saturated sodium chloride solution, dried over Na2SO4, concentrated and purified by means of RP-HPLC (acetonitrile/water). Yield 112 mg (9%). An additional 58 mg (11% yield) of 3-(ethoxycarbonyl)-2-methyl-4-(methylsulfanyl)-N-(1-methyltetrazol-5-yl)benzamide were obtained.

The examples listed in the tables below were prepared analogously to the abovementioned methods or are obtainable analogously to the abovementioned methods. The compounds listed in the tables below are very particularly preferred.

The abbreviations used mean:
Et=ethyl  Me=methyl  n-Pr=n-propyl  i-Pr=isopropyl c-Pr=cyclopropyl Ph=phenyl

TABLE 1

Inventive compounds of the formula (I) in which Q is Q1, W is C—Y, R is substituted phenyl and $R^6$ is methyl.

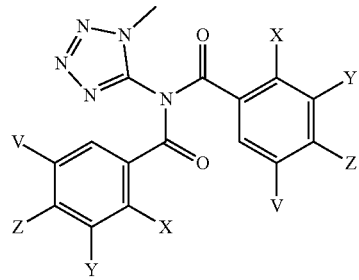

| No. | X | Y | Z | V | Physical data ($^1$H-NMR, DMSO-$d_6$, 400 MHz) |
|-----|---|---|---|---|---|
| 1-1 | F | H | Cl | H | |
| 1-2 | F | H | SO$_2$Me | H | |
| 1-3 | F | H | SO$_2$Et | H | |

TABLE 1-continued

Inventive compounds of the formula (I) in which Q is Q1, W is C—Y, R is substituted phenyl and $R^6$ is methyl.

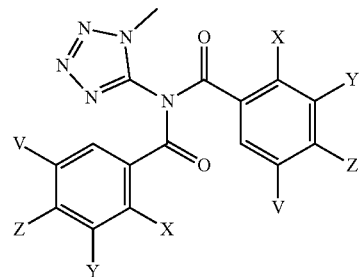

| No. | X | Y | Z | V | Physical data ($^1$H-NMR, DMSO-$d_6$, 400 MHz) |
|---|---|---|---|---|---|
| 1-4 | F | H | $CF_3$ | H | |
| 1-5 | F | H | $NO_2$ | H | |
| 1-6 | Cl | H | Br | H | |
| 1-7 | Cl | H | SMe | H | |
| 1-8 | Cl | H | SOMe | H | |
| 1-9 | Cl | H | $SO_2Me$ | H | |
| 1-10 | Cl | H | $SO_2CH_2Cl$ | H | |
| 1-11 | Cl | H | SEt | H | |
| 1-12 | Cl | H | $SO_2Et$ | H | |
| 1-13 | Cl | H | $CF_3$ | H | |
| 1-14 | Cl | H | $NO_2$ | H | |
| 1-15 | Cl | H | pyrazol-1-yl | H | |
| 1-16 | Cl | H | 1H-1,2,4-triazol-1-yl | H | |
| 1-17 | Br | H | Cl | H | |
| 1-18 | Br | H | Br | H | |
| 1-19 | Br | H | $SO_2Me$ | H | |
| 1-20 | Br | H | $SO_2Et$ | H | |
| 1-21 | Br | H | $CF_3$ | H | |
| 1-22 | $SO_2Me$ | H | Cl | H | |
| 1-23 | $SO_2Me$ | H | Br | H | |
| 1-24 | $SO_2Me$ | H | SMe | H | |
| 1-25 | $SO_2Me$ | H | SOMe | H | |
| 1-26 | $SO_2Me$ | H | $SO_2Me$ | H | |
| 1-27 | $SO_2Me$ | H | $SO_2Et$ | H | |
| 1-28 | $SO_2Me$ | H | $CF_3$ | H | 8.38 (s, 2H), 8.30 (d, 2H), 8.21 (brs, 2H), 4.20 (s, 3H), 3.41 (s, 6H), 2.22 (s, 3H) |
| 1-29 | $SO_2Et$ | H | Cl | H | |
| 1-30 | $SO_2Et$ | H | Br | H | |
| 1-31 | $SO_2Et$ | H | SMe | H | |
| 1-32 | $SO_2Et$ | H | SOMe | H | |
| 1-33 | $SO_2Et$ | H | $SO_2Me$ | H | |
| 1-34 | $SO_2Et$ | H | $CF_3$ | H | |
| 1-35 | $NO_2$ | H | F | H | |
| 1-36 | $NO_2$ | H | Cl | H | |
| 1-37 | $NO_2$ | H | Br | H | |
| 1-38 | $NO_2$ | H | I | H | |
| 1-39 | $NO_2$ | H | CN | H | |
| 1-40 | $NO_2$ | H | $SO_2Me$ | H | |
| 1-41 | $NO_2$ | H | $SO_2Et$ | H | |
| 1-42 | $NO_2$ | H | $CF_3$ | H | |
| 1-43 | Me | H | Cl | H | |
| 1-44 | Me | H | Br | H | |
| 1-45 | Me | H | SMe | H | |
| 1-46 | Me | H | $SO_2Me$ | H | |
| 1-47 | Me | H | $SO_2CH_2Cl$ | H | |
| 1-48 | Me | H | SEt | H | |
| 1-49 | Me | H | $SO_2Et$ | H | |
| 1-50 | Me | H | $CF_3$ | H | |
| 1-51 | $CH_2SO_2Me$ | H | $CF_3$ | H | |
| 1-52 | Et | H | Cl | H | |
| 1-53 | Et | H | Br | H | |
| 1-54 | Et | H | SMe | H | |
| 1-55 | Et | H | $SO_2Me$ | H | |
| 1-56 | Et | H | $SO_2CH_2Cl$ | H | |
| 1-57 | Et | H | SEt | H | |
| 1-58 | Et | H | $SO_2Et$ | H | |
| 1-59 | Et | H | $CF_3$ | H | |
| 1-60 | $CF_3$ | H | Cl | H | |
| 1-61 | $CF_3$ | H | Br | H | |

TABLE 1-continued

Inventive compounds of the formula (I) in which Q is Q1, W is C—Y, R is substituted phenyl and $R^6$ is methyl.

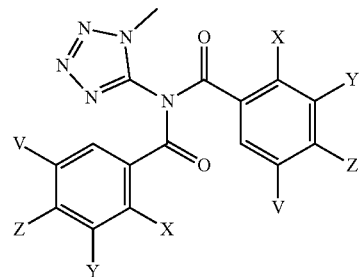

| No. | X | Y | Z | V | Physical data ($^1$H-NMR, DMSO-$d_6$, 400 MHz) |
|---|---|---|---|---|---|
| 1-62 | $CF_3$ | H | $SO_2Me$ | H | |
| 1-63 | $CF_3$ | H | $SO_2Et$ | H | |
| 1-64 | $CF_3$ | H | $CF_3$ | H | |
| 1-65 | $NO_2$ | $NH_2$ | F | H | |
| 1-66 | $NO_2$ | NHMe | F | H | |
| 1-67 | $NO_2$ | $NMe_2$ | F | H | |
| 1-68 | $NO_2$ | Me | Cl | H | |
| 1-69 | $NO_2$ | $NH_2$ | Cl | H | |
| 1-70 | $NO_2$ | NHMe | Cl | H | |
| 1-71 | $NO_2$ | $NMe_2$ | Cl | H | |
| 1-72 | $NO_2$ | $NH_2$ | Br | H | |
| 1-73 | $NO_2$ | NHMe | Br | H | |
| 1-74 | $NO_2$ | $NMe_2$ | Br | H | |
| 1-75 | $NO_2$ | $NH_2$ | $CF_3$ | H | |
| 1-76 | $NO_2$ | $NMe_2$ | $CF_3$ | H | |
| 1-77 | $NO_2$ | $NH_2$ | $SO_2Me$ | H | |
| 1-78 | $NO_2$ | $NH_2$ | $SO_2Et$ | H | |
| 1-79 | $NO_2$ | NHMe | $SO_2Me$ | H | |
| 1-80 | $NO_2$ | $NMe_2$ | $SO_2Me$ | H | |
| 1-81 | $NO_2$ | $NMe_2$ | $SO_2Et$ | H | |
| 1-82 | $NO_2$ | $NH_2$ | 1H-1,2,4-triazol-1-yl | H | |
| 1-83 | $NO_2$ | NHMe | 1H-1,2,4-triazol-1-yl | H | |
| 1-84 | $NO_2$ | $NMe_2$ | 1H-1,2,4-triazol-1-yl | H | |
| 1-85 | Me | SMe | H | H | $^1$H-NMR (400.1 MHz, $CDCl_3$): 7.518 (0.8); 7.325 (1.0); 7.320 (1.2); 7.310 (0.4); 7.306 (2.3); 7.301 (2.3); 7.280 (2.0); 7.272 (0.3); 7.2694 (0.4); 7.2687 (0.4); 7.268 (0.5); 7.266 (0.7); 7.265 (0.9); 7.259 (133.8); 7.242 (1.8); 7.170 (1.5); 7.166 (1.6); 7.150 (1.1); 7.146 (1.1); 6.995 (0.7); 5.298 (1.0); 4.107 (9.8); 2.446 (16.0); 1.527 (33.0); 0.008 (1.6) |
| 1-86 | Me | SOMe | H | H | 8.10-8.06 (m, 2H), 7.69-7.60 (m, 4H), 4.10 (s, 3H), 2.79 (s, 6H), |
| 1-87 | Me | $SO_2Me$ | H | H | |
| 1-88 | Me | SEt | H | H | |
| 1-89 | Me | SOEt | H | H | |
| 1-90 | Me | $SO_2Et$ | H | H | |
| 1-91 | Me | $S(CH_2)_2OMe$ | H | H | |
| 1-92 | Me | $SO(CH_2)_2OMe$ | H | H | |
| 1-93 | Me | $SO_2(CH_2)_2OMe$ | H | H | |
| 1-94 | Me | F | F | H | |
| 1-95 | Me | F | SMe | H | |
| 1-96 | Me | SEt | F | H | |
| 1-97 | Me | SOEt | F | H | |
| 1-98 | Me | $SO_2Et$ | F | H | |
| 1-99 | Me | Me | Cl | H | |
| 1-100 | Me | F | Cl | H | |
| 1-101 | Me | Cl | Cl | H | |
| 1-102 | Me | $NH_2$ | Cl | H | |
| 1-103 | Me | NHMe | Cl | H | |
| 1-104 | Me | $NMe_2$ | Cl | H | |
| 1-105 | Me | $O(CH_2)_2OMe$ | Cl | H | |
| 1-106 | Me | $O(CH_2)_3OMe$ | Cl | H | |

TABLE 1-continued

Inventive compounds of the formula (I) in which Q is Q1, W is C—Y, R is substituted phenyl and $R^6$ is methyl.

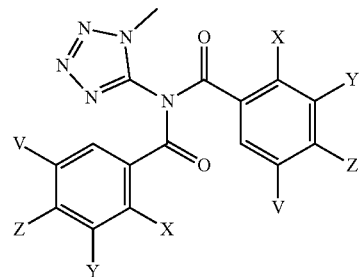

| No. | X | Y | Z | V | Physical data ($^1$H-NMR, DMSO-$d_6$, 400 MHz) |
|---|---|---|---|---|---|
| 1-107 | Me | O(CH$_2$)$_4$OMe | Cl | H | |
| 1-108 | Me | OCH$_2$CONMe$_2$ | Cl | H | |
| 1-109 | Me | O(CH$_2$)$_2$—CO—NMe$_2$ | Cl | H | |
| 1-110 | Me | O(CH$_2$)$_2$—NH(CO)NMe$_2$ | Cl | H | |
| 1-111 | Me | O(CH$_2$)$_2$—NH(CO)NHCO$_2$Et | Cl | H | |
| 1-112 | Me | O(CH$_2$)$_2$—NHCO$_2$Me | Cl | H | |
| 1-113 | Me | OCH$_2$—NHSO$_2$cPr | Cl | H | |
| 1-114 | Me | O(CH$_2$)-5-2,4-dimethyl-2,4-dihydro-3H-1,2,4-triazol-3-one | Cl | H | |
| 1-115 | Me | O(CH$_2$)-3,5-dimethyl-1,2-oxazol-4-yl | Cl | H | |
| 1-116 | Me | SMe | Cl | H | |
| 1-117 | Me | SOMe | Cl | H | |
| 1-118 | Me | SO$_2$Me | Cl | H | |
| 1-119 | Me | SEt | Cl | H | |
| 1-120 | Me | SOEt | Cl | H | |
| 1-121 | Me | SO$_2$Et | Cl | H | |
| 1-122 | Me | S(CH$_2$)$_2$OMe | Cl | H | |
| 1-123 | Me | SO(CH$_2$)$_2$OMe | Cl | H | |
| 1-124 | Me | SO$_2$(CH$_2$)$_2$OMe | Cl | H | |
| 1-125 | Me | NH$_2$ | Br | H | |
| 1-126 | Me | NHMe | Br | H | |
| 1-127 | Me | NMe$_2$ | Br | H | |
| 1-128 | Me | OCH$_2$(CO)NMe$_2$ | Br | H | |
| 1-129 | Me | O(CH$_2$)-5-pyrrolidin-2-one | Br | H | |
| 1-130 | Me | SMe | Br | H | |
| 1-131 | Me | SOMe | Br | H | |
| 1-132 | Me | SO$_2$Me | Br | H | |
| 1-133 | Me | SEt | Br | H | |
| 1-134 | Me | SOEt | Br | H | |
| 1-135 | Me | SO$_2$Et | Br | H | |
| 1-136 | Me | SMe | I | H | |
| 1-137 | Me | SOMe | I | H | |
| 1-138 | Me | SO$_2$Me | I | H | |
| 1-139 | Me | SEt | I | H | |
| 1-140 | Me | SOEt | I | H | |
| 1-141 | Me | SO$_2$Et | I | H | |
| 1-142 | Me | Cl | CF$_3$ | H | |
| 1-143 | Me | SMe | CF$_3$ | H | |
| 1-144 | Me | SOMe | CF$_3$ | H | |
| 1-145 | Me | SO$_2$Me | CF$_3$ | H | |
| 1-146 | Me | SEt | CF$_3$ | H | |
| 1-147 | Me | SOEt | CF$_3$ | H | |
| 1-148 | Me | SO$_2$Et | CF$_3$ | H | |
| 1-149 | Me | S(CH$_2$)$_2$OMe | CF$_3$ | H | |
| 1-150 | Me | SO$_2$(CH$_2$)$_2$OMe | CF$_3$ | H | |
| 1-151 | Me | SO$_2$(CH$_2$)$_2$OMe | CF$_3$ | H | |
| 1-152 | Me | Me | SO$_2$Me | H | |
| 1-153 | Me | 4,5-dihydro-1,2-oxazol-3-yl | SO$_2$Me | H | |
| 1-154 | Me | 4,5-dihydro-1,2-oxazol-3-yl | SO$_2$Et | H | |
| 1-155 | Me | 5-cyanomethyl-4,5-dihydro-1,2-oxazol-3-yl | SO$_2$Me | H | |

TABLE 1-continued

Inventive compounds of the formula (I) in which Q is Q1, W is C—Y, R is substituted phenyl and $R^6$ is methyl.

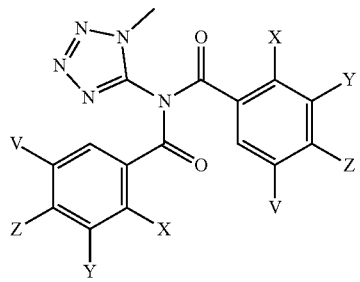

| No. | X | Y | Z | V | Physical data ($^1$H-NMR, DMSO-$d_6$, 400 MHz) |
|---|---|---|---|---|---|
| 1-156 | Me | 5-cyanomethyl-4,5-dihydro-1,2-oxazol-3-yl | $SO_2Et$ | H | |
| 1-157 | Me | $NH_2$ | $SO_2Me$ | H | |
| 1-158 | Me | NHMe | $SO_2Me$ | H | |
| 1-159 | Me | $NMe_2$ | $SO_2Me$ | H | |
| 1-160 | Me | $NH(CH_2)_2OMe$ | $SO_2Me$ | H | |
| 1-161 | Me | pyrazol-1-yl | $SO_2Me$ | H | |
| 1-162 | Me | OH | $SO_2Me$ | H | |
| 1-163 | Me | OMe | $SO_2Me$ | H | |
| 1-164 | Me | OMe | $SO_2Et$ | H | |
| 1-165 | Me | OEt | $SO_2Me$ | H | |
| 1-166 | Me | OEt | $SO_2Et$ | H | |
| 1-167 | Me | O-i-Pr | $SO_2Me$ | H | |
| 1-168 | Me | O-i-Pr | $SO_2Et$ | H | |
| 1-169 | Me | $O(CH_2)_2OMe$ | $SO_2Me$ | H | |
| 1-170 | Me | $O(CH_2)_2OMe$ | $SO_2Et$ | H | |
| 1-171 | Me | $O(CH_2)_3OMe$ | $SO_2Me$ | H | |
| 1-172 | Me | $O(CH_2)_3OMe$ | $SO_2Et$ | H | |
| 1-173 | Me | $O(CH_2)_4OMe$ | $SO_2Me$ | H | |
| 1-174 | Me | $O(CH_2)_4OMe$ | $SO_2Et$ | H | |
| 1-175 | Me | $O(CH_2)_2NHSO2Me$ | $SO_2Me$ | H | |
| 1-176 | Me | $O(CH_2)_2NHSO2Me$ | $SO_2Et$ | H | |
| 1-177 | Me | $OCH_2(CO)NMe_2$ | $SO_2Me$ | H | |
| 1-178 | Me | $OCH_2(CO)NMe_2$ | $SO_2Et$ | H | |
| 1-179 | Me | [1,4]dioxan-2-ylmethoxy | $SO_2Me$ | H | |
| 1-180 | Me | [1,4]dioxan-2-ylmethoxy | $SO_2Et$ | H | |
| 1-181 | Me | $O(CH_2)_2$—O-(3,5-di methoxypyrimidin-2-yl) | $SO_2Me$ | H | |
| 1-182 | Me | Cl | $SO_2Me$ | H | |
| 1-183 | Me | SMe | $SO_2Me$ | H | |
| 1-184 | Me | SOMe | $SO_2Me$ | H | |
| 1-185 | Me | $SO_2Me$ | $SO_2Me$ | H | |
| 1-186 | Me | $SO_2Me$ | $SO_2Et$ | H | |
| 1-187 | Me | SEt | $SO_2Me$ | H | |
| 1-188 | Me | SOEt | $SO_2Me$ | H | |
| 1-189 | Me | $SO_2Et$ | $SO_2Me$ | H | |
| 1-190 | Me | $S(CH_2)_2OMe$ | $SO_2Me$ | H | |
| 1-191 | Me | $SO(CH_2)_2OMe$ | $SO_2Me$ | H | |
| 1-192 | Me | $SO_2(CH_2)_2OMe$ | SO2Me | H | |
| 1-193 | $CH_2SMe$ | OMe | $SO_2Me$ | H | |
| 1-194 | $CH_2OMe$ | OMe | $SO_2Me$ | H | |
| 1-195 | $CH_2O(CH_2)_2OMe$ | $NH(CH_2)_2OEt$ | $SO_2Me$ | H | |
| 1-196 | $CH_2O(CH_2)_2OMe$ | $NH(CH_2)_3OEt$ | $SO_2Me$ | H | |
| 1-197 | $CH_2O(CH_2)_3OMe$ | OMe | $SO_2Me$ | H | |
| 1-198 | $CH_2O(CH_2)_2OMe$ | $NH(CH_2)_2OMe$ | $SO_2Me$ | H | |
| 1-199 | $CH_2O(CH_2)_2OMe$ | $NH(CH_2)_3OMe$ | $SO_2Me$ | H | |
| 1-200 | Et | SMe | Cl | H | |
| 1-201 | Et | $SO_2Me$ | Cl | H | |
| 1-202 | Et | SMe | $CF_3$ | H | |
| 1-203 | Et | $SO_2Me$ | $CF_3$ | H | |
| 1-204 | Et | F | $SO_2Me$ | H | |
| 1-205 | Et | $NH(CH_2)_2OMe$ | $SO_2Me$ | H | |
| 1-206 | i-Pr | $SO_2Me$ | $CF_3$ | H | $^1$H-NMR (400.1 MHz, CDCl$_3$): 7.821 (1.6); 7.801 (1.9); 7.593 (0.8); 7.575 (0.7); 7.263 (18.6); 7.260 (18.8); 5.301 (6.9); 5.298 (7.1); 4.312 (0.3); 4.295 (0.8); |

TABLE 1-continued

Inventive compounds of the formula (I) in which Q is Q1, W is C—Y, R is substituted phenyl and $R^6$ is methyl.

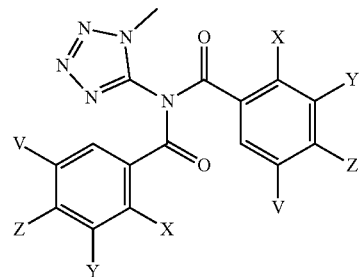

| No. | X | Y | Z | V | Physical data ($^1$H-NMR, DMSO-$d_6$, 400 MHz) |
|---|---|---|---|---|---|
|  |  |  |  |  | 4.277 (1.1); 4.260 (0.8); 4.242 (0.4); 4.133 (0.4); 4.131 (0.5); 4.120 (8.4); 4.117 (8.5); 3.335 (15.8); 3.334 (16.0); 3.266 (1.0); 3.264 (1.0); 3.196 (0.8); 3.194 (0.8); 2.046 (1.5); 2.044 (1.5); 1.714 (0.4); 1.643 (0.4); 1.640 (0.5); 1.625 (0.4); 1.623 (0.4); 1.521 (12.5); 1.503 (12.3); 1.395 (0.5); 1.393 (0.5); 1.378 (0.4); 1.375 (0.4); 1.294 (0.5); 1.292 (0.5); 1.279 (0.6); 1.277 (0.9); 1.262 (1.0); 1.259 (1.1); 1.244 (0.4); 1.241 (0.5); 0.003 (8.2); 0.000 (8.9) |
| 1-207 | cPr | SO$_2$Me | CF$_3$ | H |  |
| 1-208 | CF$_3$ | O(CH$_2$)$_2$OMe | F | H |  |
| 1-209 | CF$_3$ | O(CH$_2$)$_3$OMe | F | H |  |
| 1-210 | CF$_3$ | OCH$_2$CONMe$_2$ | F | H |  |
| 1-211 | CF$_3$ | [1,4]dioxan-2-ylmethoxy | F | H |  |
| 1-212 | CF$_3$ | O(CH$_2$)$_2$OMe | Cl | H |  |
| 1-213 | CF$_3$ | O(CH$_2$)$_3$OMe | Cl | H |  |
| 1-214 | CF$_3$ | OCH$_2$CONMe$_2$ | Cl | H |  |
| 1-215 | CF$_3$ | [1,4]dioxan-2-ylmethoxy | Cl | H |  |
| 1-216 | CF$_3$ | O(CH$_2$)$_2$OMe | Br | H |  |
| 1-217 | CF$_3$ | O(CH$_2$)$_3$OMe | Br | H |  |
| 1-218 | CF$_3$ | OCH$_2$CONMe$_2$ | Br | H |  |
| 1-219 | CF$_3$ | [1,4]dioxan-2-ylmethoxy | Br | H |  |
| 1-220 | CF$_3$ | O(CH$_2$)$_2$OMe | I | H |  |
| 1-221 | CF$_3$ | O(CH$_2$)$_3$OMe | I | H |  |
| 1-222 | CF$_3$ | OCH$_2$CONMe$_2$ | I | H |  |
| 1-223 | CF$_3$ | [1,4]dioxan-2-ylmethoxy | I | H |  |
| 1-224 | CF$_3$ | F | SO$_2$Me | H |  |
| 1-225 | CF$_3$ | F | SO$_2$Et | H |  |
| 1-226 | CF$_3$ | O(CH$_2$)$_2$OMe | SO$_2$Me | H |  |
| 1-227 | CF$_3$ | O(CH$_2$)$_2$OMe | SO$_2$Et | H |  |
| 1-228 | CF$_3$ | O(CH$_2$)$_3$OMe | SO$_2$Me | H |  |
| 1-229 | CF$_3$ | O(CH$_2$)$_3$OMe | SO$_2$Et | H |  |
| 1-230 | CF$_3$ | OCH$_2$CONMe$_2$ | SO$_2$Me | H |  |
| 1-231 | CF$_3$ | OCH$_2$CONMe$_2$ | SO$_2$Et | H |  |
| 1-232 | CF$_3$ | [1,4]dioxan-2-ylmethoxy | SO$_2$Me | H |  |
| 1-233 | CF$_3$ | [1,4]dioxan-2-ylmethoxy | SO$_2$Et | H |  |
| 1-234 | F | SMe | CF$_3$ | H |  |
| 1-235 | F | SOMe | CF$_3$ | H |  |
| 1-236 | Cl | Me | Cl | H |  |
| 1-237 | Cl | OCH$_2$CHCH$_2$ | Cl | H |  |
| 1-238 | Cl | OCH$_2$CHF$_2$ | Cl | H |  |
| 1-239 | Cl | O(CH$_2$)$_2$OMe | Cl | H |  |
| 1-240 | Cl | OCH$_2$CONMe$_2$ | Cl | H |  |
| 1-241 | Cl | O(CH$_2$)-5-pyrrolidin-2-one | Cl | H |  |
| 1-242 | Cl | SMe | Cl | H |  |
| 1-243 | Cl | SOMe | Cl | H |  |
| 1-244 | Cl | SO$_2$Me | Cl | H |  |
| 1-245 | Cl | F | SMe | H |  |

TABLE 1-continued

Inventive compounds of the formula (I) in which Q is Q1, W is C—Y, R is substituted phenyl and $R^6$ is methyl.

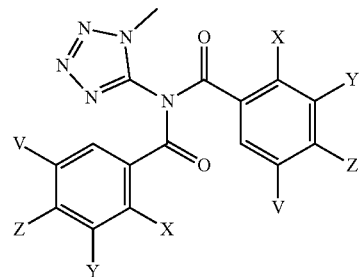

| No. | X | Y | Z | V | Physical data ($^1$H-NMR, DMSO-$d_6$, 400 MHz) |
|---|---|---|---|---|---|
| 1-246 | Cl | Cl | $SO_2Me$ | H | |
| 1-247 | Cl | $CO_2Me$ | $SO_2Me$ | H | |
| 1-248 | Cl | $CONMe_2$ | $SO_2Me$ | H | |
| 1-249 | Cl | CONMe(OMe) | $SO_2Me$ | H | |
| 1-250 | Cl | $CH_2OMe$ | $SO_2Me$ | H | |
| 1-251 | Cl | $CH_2OMe$ | $SO_2Et$ | H | |
| 1-252 | Cl | $CH_2OEt$ | $SO_2Me$ | H | |
| 1-253 | Cl | $CH_2OEt$ | $SO_2Et$ | H | |
| 1-254 | Cl | $CH_2OCH_2CHF_2$ | $SO_2Me$ | H | |
| 1-255 | Cl | $CH_2OCH_2CF_3$ | $SO_2Me$ | H | |
| 1-256 | Cl | $CH_2OCH_2CF_3$ | $SO_2Et$ | H | |
| 1-257 | Cl | $CH_2OCH_2CF_2CHF_2$ | $SO_2Me$ | H | |
| 1-258 | Cl | $CH_2OcPentyl$ | $SO_2Me$ | H | |
| 1-259 | Cl | $CH_2PO(OMe)_2$ | $SO_2Me$ | H | |
| 1-260 | Cl | 4,5-dihydro-1,2-oxazol-3-yl | SMe | H | |
| 1-261 | Cl | 4,5-dihydro-1,2-oxazol-3-yl | $SO_2Me$ | H | |
| 1-262 | Cl | 4,5-dihydro-1,2-oxazol-3-yl | $SO_2Et$ | H | |
| 1-263 | Cl | 5-cyanomethyl-4,5-dihydro-1,2-oxazol-3-yl | $SO_2Me$ | H | |
| 1-264 | Cl | 5-cyanomethyl-4,5-dihydro-1,2-oxazol-3-yl | $SO_2Et$ | H | |
| 1-265 | Cl | 5-(methoxymethyl)-4,5-dihydro-1,2-oxazol-3-yl | $SO_2Et$ | H | |
| 1-266 | Cl | 5-(methoxymethyl)-5-methyl-4,5-dihydro-1,2-oxazol-3-yl | $SO_2Et$ | H | |
| 1-267 | Cl | $CH_2O$-tetrahydrofuran-3-yl | $SO_2Me$ | H | |
| 1-268 | Cl | $CH_2O$-tetrahydrofuran-3-yl | $SO_2Et$ | | |
| 1-269 | Cl | $CH_2OCH_2$-tetrahydrofuran-2-yl | $SO_2Me$ | H | |
| 1-270 | Cl | $CH_2OCH_2$-tetrahydrofuran-2-yl | $SO_2Et$ | H | |
| 1-271 | Cl | $CH_2OCH_2$-tetrahydrofuran-3-yl | $SO_2Me$ | H | |
| 1-272 | Cl | $CH_2OCH_2$-tetrahydrofuran-3-yl | $SO_2Et$ | H | |
| 1-273 | Cl | OMe | $SO_2Me$ | H | |
| 1-274 | Cl | OMe | $SO_2Et$ | H | |
| 1-275 | Cl | OEt | $SO_2Me$ | H | |
| 1-276 | Cl | OEt | $SO_2Et$ | H | |
| 1-277 | Cl | O-i-Pr | $SO_2Me$ | H | |
| 1-278 | Cl | O-i-Pr | $SO_2Et$ | H | |
| 1-279 | Cl | $O(CH_2)_2OMe$ | $SO_2Me$ | H | |
| 1-280 | Cl | $O(CH_2)_4OMe$ | $SO_2Me$ | H | |
| 1-281 | Cl | $O(CH_2)_4OMe$ | $SO_2Et$ | H | |
| 1-282 | Cl | $O(CH_2)_3OMe$ | $SO_2Me$ | H | |
| 1-283 | Cl | $O(CH_2)_3OMe$ | $SO_2Et$ | H | |
| 1-284 | Cl | $O(CH_2)_2OMe$ | $SO_2Me$ | H | |
| 1-285 | Cl | $O(CH_2)_2OMe$ | $SO_2Et$ | H | |
| 1-286 | Cl | [1,4]dioxan-2-ylmethoxy | $SO_2Me$ | H | |

TABLE 1-continued

Inventive compounds of the formula (I) in which Q is Q1, W is C—Y, R is substituted phenyl and $R^6$ is methyl.

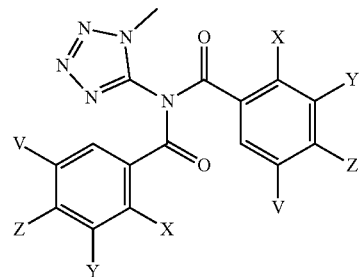

| No. | X | Y | Z | V | Physical data ($^1$H-NMR, DMSO-$d_6$, 400 MHz) |
|---|---|---|---|---|---|
| 1-287 | Cl | [1,4]dioxan-2-ylmethoxy | SO$_2$Et | H | |
| 1-288 | Cl | OCH$_2$(CO)NMe$_2$ | SO$_2$Me | H | |
| 1-289 | Cl | OCH$_2$(CO)NMe$_2$ | SO$_2$Et | H | |
| 1-290 | Cl | SMe | SO$_2$Me | H | |
| 1-291 | Cl | SOMe | SO$_2$Me | H | |
| 1-292 | Br | OMe | Br | H | |
| 1-293 | Br | O(CH$_2$)$_2$OMe | Br | H | |
| 1-294 | Br | O(CH$_2$)$_2$OMe | SO$_2$Me | H | |
| 1-295 | Br | O(CH$_2$)$_2$OMe | SO$_2$Et | H | |
| 1-296 | Br | O(CH$_2$)$_3$OMe | SO$_2$Me | H | |
| 1-297 | Br | O(CH$_2$)$_3$OMe | SO$_2$Et | H | |
| 1-298 | Br | O(CH$_2$)$_4$OMe | SO$_2$Me | H | |
| 1-299 | Br | O(CH$_2$)$_4$OMe | SO$_2$Et | H | |
| 1-300 | Br | [1,4]dioxan-2-ylmethoxy | SO$_2$Me | H | |
| 1-301 | Br | [1,4]dioxan-2-ylmethoxy | SO$_2$Et | H | |
| 1-302 | I | O(CH$_2$)$_2$OMe | SO$_2$Me | H | |
| 1-303 | I | O(CH$_2$)$_2$OMe | SO$_2$Et | H | |
| 1-304 | I | O(CH$_2$)$_3$OMe | SO$_2$Me | H | |
| 1-305 | I | O(CH$_2$)$_3$OMe | SO$_2$Et | H | |
| 1-306 | I | O(CH$_2$)$_4$OMe | SO$_2$Me | H | |
| 1-307 | I | O(CH$_2$)$_4$OMe | SO$_2$Et | H | |
| 1-308 | I | [1,4]dioxan-2-ylmethoxy | SO$_2$Me | H | |
| 1-309 | I | [1,4]dioxan-2-ylmethoxy | SO$_2$Et | H | |
| 1-310 | OMe | SMe | CF$_3$ | H | |
| 1-311 | OMe | SOMe | CF$_3$ | H | |
| 1-312 | OMe | SO$_2$Me | CF$_3$ | H | |
| 1-313 | OMe | SOEt | CF$_3$ | H | |
| 1-314 | OMe | SO$_2$Et | CF$_3$ | H | |
| 1-315 | OMe | S(CH$_2$)$_2$OMe | CF$_3$ | H | |
| 1-316 | OMe | SO(CH$_2$)$_2$OMe | CF$_3$ | H | |
| 1-317 | OMe | SO$_2$(CH$_2$)$_2$OMe | CF$_3$ | H | |
| 1-318 | OMe | SMe | Cl | H | |
| 1-319 | OMe | SOMe | Cl | H | |
| 1-320 | OMe | SO$_2$Me | Cl | H | |
| 1-321 | OMe | SEt | Cl | H | |
| 1-322 | OMe | SOEt | Cl | H | |
| 1-323 | OMe | SO2Et | Cl | H | |
| 1-324 | OMe | S(CH$_2$)$_2$OMe | Cl | H | |
| 1-325 | OMe | SO(CH$_2$)$_2$OMe | Cl | H | |
| 1-326 | OMe | SO$_2$(CH$_2$)$_2$OMe | Cl | H | |
| 1-327 | OCH$_2$c-Pr | SMe | CF$_3$ | H | |
| 1-328 | OCH$_2$c-Pr | SOMe | CF$_3$ | H | |
| 1-329 | OCH$_2$c-Pr | SO$_2$Me | CF$_3$ | H | |
| 1-330 | OCH$_2$c-Pr | SEt | CF$_3$ | H | |
| 1-331 | OCH$_2$c-Pr | SOEt | CF$_3$ | H | |
| 1-332 | OCH$_2$c-Pr | SO$_2$Et | CF$_3$ | H | |
| 1-333 | OCH$_2$c-Pr | S(CH$_2$)$_2$OMe | CF$_3$ | H | |
| 1-334 | OCH$_2$c-Pr | SO(CH$_2$)$_2$OMe | CF$_3$ | H | |
| 1-335 | OCH$_2$c-Pr | SO$_2$(CH$_2$)$_2$OMe | CF$_3$ | H | |
| 1-336 | OCH$_2$c-Pr | SMe | Cl | H | |
| 1-337 | OCH$_2$c-Pr | SOMe | Cl | H | |
| 1-338 | OCH$_2$c-Pr | SO$_2$Me | Cl | H | |
| 1-339 | OCH$_2$c-Pr | SEt | Cl | H | |
| 1-340 | OCH$_2$c-Pr | SOEt | Cl | H | |
| 1-341 | OCH$_2$c-Pr | SO$_2$Et | Cl | H | |
| 1-342 | OCH$_2$c-Pr | S(CH$_2$)$_2$OMe | Cl | H | |

TABLE 1-continued

Inventive compounds of the formula (I) in which Q is Q1, W is C—Y, R is substituted phenyl and $R^6$ is methyl.

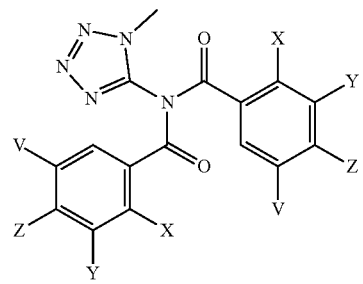

| No. | X | Y | Z | V | Physical data ($^1$H-NMR, DMSO-$d_6$, 400 MHz) |
|---|---|---|---|---|---|
| 1-343 | OCH$_2$c-Pr | SO(CH$_2$)$_2$OMe | Cl | H | |
| 1-344 | OCH$_2$c-Pr | SO$_2$(CH$_2$)$_2$OMe | Cl | H | |
| 1-345 | OCH$_2$c-Pr | SMe | SO$_2$Me | H | |
| 1-346 | OCH$_2$c-Pr | SOMe | SO$_2$Me | H | |
| 1-347 | OCH$_2$c-Pr | SO$_2$Me | SO$_2$Me | H | |
| 1-348 | OCH$_2$c-Pr | SEt | SO$_2$Me | H | |
| 1-349 | OCH$_2$c-Pr | SOEt | SO$_2$Me | H | |
| 1-350 | OCH$_2$c-Pr | SO$_2$Et | SO$_2$Me | H | |
| 1-351 | OCH$_2$c-Pr | S(CH$_2$)$_2$OMe | SO$_2$Me | H | |
| 1-352 | OCH$_2$c-Pr | SO(CH$_2$)$_2$OMe | SO$_2$Me | H | |
| 1-353 | OCH$_2$c-Pr | SO$_2$(CH$_2$)$_2$OMe | SO$_2$Me | H | |
| 1-354 | SO$_2$Me | F | CF$_3$ | H | |
| 1-355 | SO$_2$Me | NH$_2$ | CF$_3$ | H | |
| 1-356 | SO$_2$Me | NHEt | Cl | H | |
| 1-357 | SMe | SEt | F | H | |
| 1-358 | SMe | SMe | F | H | |
| 1-359 | SMe | SMe | CF$_3$ | H | |
| 1-360 | SMe | SOMe | CF$_3$ | H | |
| 1-361 | SMe | SO$_2$Me | CF$_3$ | H | |
| 1-362 | SMe | SMe | Cl | H | |
| 1-363 | SMe | SMe | Br | H | |
| 1-364 | Cl | Ac | CF$_3$ | H | |
| 1-365 | Cl | Ac | SO$_2$Me | H | |
| 1-366 | Cl | C(O)cPr | CF$_3$ | H | |
| 1-367 | Cl | C(O)cPr | SO$_2$Me | H | |
| 1-368 | Cl | CH$_2$SMe | CF$_3$ | H | |
| 1-369 | Cl | CH$_2$S(O)Me | CF$_3$ | H | |
| 1-370 | Cl | CH$_2$SO$_2$Me | CF$_3$ | H | |
| 1-371 | Cl | CH$_2$SMe | SO$_2$Me | H | |
| 1-372 | Cl | CH$_2$S(O)Me | SO$_2$Me | H | |
| 1-373 | Cl | CH$_2$SO$_2$Me | SO$_2$Me | H | |
| 1-374 | Cl | CH=NOMe | CF$_3$ | H | |
| 1-375 | Cl | CH=NOMe | SO$_2$Me | H | |
| 1-376 | Cl | 4,5-dihydro-1,2-oxazol-5-yl, | CF$_3$ | H | |
| 1-377 | Cl | 4,5-dihydro-1,2-oxazol-5-yl, | SO$_2$Me | H | |
| 1-378 | Cl | 3-methyl-4,5-dihydro-1,2-oxazol-5-yl | CF$_3$ | H | |
| 1-379 | Cl | 3-methyl-4,5-dihydro-1,2-oxazol-5-yl | SO$_2$Me | H | |
| 1-380 | Cl | vinyl | CF$_3$ | H | |
| 1-381 | Cl | vinyl | SO$_2$Me | H | |
| 1-382 | Cl | CO$_2$Me | CF$_3$ | H | |
| 1-383 | Cl | CO$_2$Me | SO$_2$Me | H | |
| 1-384 | Cl | SMe | CF$_3$ | H | |
| 1-385 | Cl | S(O)Me | CF$_3$ | H | |
| 1-386 | Cl | SO$_2$Me | CF$_3$ | H | |
| 1-387 | Cl | SO$_2$Me | SO$_2$Me | H | |
| 1-388 | Cl | SMe | Me | H | |
| 1-389 | Cl | SOMe | Me | H | |
| 1-390 | Cl | SO$_2$Me | Me | H | |
| 1-391 | Cl | 1H-1,2,4-triazol-1-yl | CF$_3$ | H | |

TABLE 1-continued

Inventive compounds of the formula (I) in which Q is Q1, W is C—Y, R is substituted phenyl and $R^6$ is methyl.

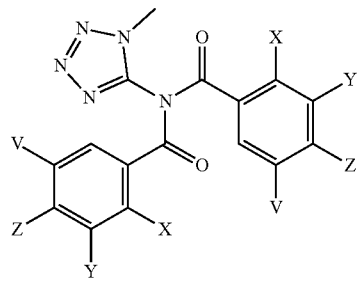

| No. | X | Y | Z | V | Physical data ($^1$H-NMR, DMSO-$d_6$, 400 MHz) |
|---|---|---|---|---|---|
| 1-392 | Cl | 1H-1,2,3-triazol-1-yl | $CF_3$ | H | |
| 1-393 | Cl | 2H-1,2,3-triazol-2-yl | $CF_3$ | H | |
| 1-394 | Cl | 1H-pyrazol-1-yl | $CF_3$ | H | |
| 1-395 | Cl | 1H-4-chloropyrazol-1-yl | $CF_3$ | H | |
| 1-396 | Cl | 1H-3-bromopyrazol-1-yl | $CF_3$ | H | |
| 1-397 | Cl | 1H-4-trifluoromethyl-pyrazol-1-yl | $CF_3$ | H | |
| 1-398 | Cl | pyrolidin-2-on-1-yl | $CF_3$ | H | |
| 1-399 | Cl | morpholin-3-on-4-yl | $CF_3$ | H | |
| 1-400 | Cl | 1,2-thiazolidine-1,1-dioxid-2-yl | $CF_3$ | H | |
| 1-401 | Br | 1H-1,2,4-triazol-1-yl | $CF_3$ | H | |
| 1-402 | Br | 1H-1,2,4-triazol-1-yl | $CF_3$ | H | |
| 1-403 | Br | 2H-1,2,3-triazol-2-yl | $CF_3$ | H | |
| 1-404 | Br | 1H-pyrazol-1-yl | $CF_3$ | H | |
| 1-405 | Br | 1H-4-chloropyrazol-1-yl | $CF_3$ | H | |
| 1-406 | Br | 1H-3-bromopyrazol-1-yl | $CF_3$ | H | |
| 1-407 | Br | 1H-4-trifluoromethyl-pyrazol-1-yl | $CF_3$ | H | |
| 1-408 | Br | pyrolidin-2-on-1-yl | $CF_3$ | H | |
| 1-409 | Br | morpholin-3-on-4-yl | $CF_3$ | H | |
| 1-410 | Br | 1,2-thiazolidine-1,1-dioxid-2-yl | $CF_3$ | H | |
| 1-411 | $CH_2OMe$ | 1H-1,2,4-triazol-1-yl | $CF_3$ | H | |
| 1-412 | $CH_2OMe$ | 1H-1,2,4-triazol-1-yl | $CF_3$ | H | |
| 1-413 | $CH_2OMe$ | 2H-1,2,3-triazol-2-yl | $CF_3$ | H | |
| 1-414 | $CF_3$ | $OCH_2CH_2F$ | $CF_3$ | H | |
| 1-415 | $CF_3$ | OMe | $CF_3$ | H | |
| 1-416 | $CF_3$ | SMe | $CF_3$ | H | |
| 1-417 | $CF_3$ | SOMe | $CF_3$ | H | |
| 1-418 | $CF_3$ | $SO_2Me$ | $CF_3$ | H | |
| 1-419 | $CF_3$ | 1H-pyrazol-1-yl | $CF_3$ | H | |
| 1-420 | Me | SMe | Et | H | |
| 1-421 | Me | SOMe | Et | H | |
| 1-422 | Me | $SO_2Me$ | Et | H | |
| 1-423 | Me | 1H-pyrazol-1-yl | Et | H | |
| 1-424 | Me | $OCH_2CH_2F$ | Et | H | |
| 1-425 | Me | OMe | Et | H | |
| 1-426 | Me | Ac | $CF_3$ | H | |
| 1-427 | Me | Ac | $SO_2Me$ | H | |
| 1-428 | Me | C(O)cPr | $CF_3$ | H | |
| 1-429 | Me | C(O)cPr | $SO_2Me$ | H | |
| 1-430 | Me | $CH_2SMe$ | $CF_3$ | H | |
| 1-431 | Me | $CH_2S(O)Me$ | $CF_3$ | H | |
| 1-432 | Me | $CH_2SO_2Me$ | $CF_3$ | H | |
| 1-433 | Me | $CH_2SMe$ | $SO_2Me$ | H | |
| 1-434 | Me | $CH_2S(O)Me$ | $SO_2Me$ | H | |
| 1-435 | Me | $CH_2SO_2Me$ | $SO_2Me$ | H | |
| 1-436 | Me | CH=NOMe | $CF_3$ | H | |
| 1-437 | Me | CH=NOMe | $SO_2Me$ | H | |
| 1-438 | Me | 4,5-dihydro-1,2-oxazol-5-yl, | $CF_3$ | H | |

TABLE 1-continued

Inventive compounds of the formula (I) in which Q is Q1, W is C—Y, R is substituted phenyl and $R^6$ is methyl.

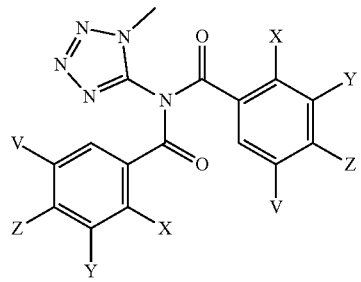

| No. | X | Y | Z | V | Physical data ($^1$H-NMR, DMSO-$d_6$, 400 MHz) |
|---|---|---|---|---|---|
| 1-439 | Me | 4,5-dihydro-1,2-oxazol-5-yl, | $SO_2Me$ | H | |
| 1-440 | Me | 3-methyl-4,5-dihydro-1,2-oxazol-5-yl | $CF_3$ | H | |
| 1-441 | Me | 3-methyl-4,5-dihydro-1,2-oxazol-5-yl | $SO_2Me$ | H | |
| 1-442 | Me | vinyl | $CF_3$ | H | |
| 1-443 | Me | vinyl | $SO_2Me$ | H | |
| 1-444 | Me | $CO_2Me$ | $CF_3$ | H | |
| 1-445 | Me | $CO_2Me$ | $SO_2Me$ | H | |
| 1-446 | Me | $CO_2Me$ | SMe | H | |
| 1-447 | Me | $NH_2$ | $CF_3$ | H | $^1$H-NMR (400.0 MHz, $CDCl_3$): 7.519 (0.7); 7.284 (2.2); 7.260 (119.6); 6.996 (0.7); 6.821 (1.9); 6.801 (1.8); 4.281 (2.5); 4.064 (15.4); 2.422 (2.3); 2.137 (16.0); 2.045 (2.1); 1.552 (1.7); 1.277 (0.7); 1.259 (1.4); 1.241 (0.6); 0.882 (0.7); 0.008 (1.3); 0.000 (39.1); −0.009 (1.1) |
| 1-448 | Me | $NMe_2$ | $CF_3$ | H | $^1$H-NMR (400.0 MHz, $CDCl_3$): 7.468 (0.9); 7.448 (1.4); 7.373 (1.2); 7.353 (0.8); 7.260 (55.6); 4.087 (7.4); 2.826 (1.4); 2.684 (16.0); 2.520 (0.7); 2.291 (8.3); 1.545 (2.5); 0.008 (0.6); 0.000 (19.2); −0.009 (0.5) |
| 1-449 | Me | NHMe | $CF_3$ | H | $^1$H-NMR (400.0 MHz, $CDCl_3$): 7.373 (1.7); 7.352 (2.0); 7.261 (33.1); 7.133 (1.7); 7.113 (1.5); 4.063 (16.0); 2.729 (10.7); 2.356 (14.5); 1.553 (1.5); 1.256 (1.2); 0.000 (12.2) |
| 1-450 | Me | $SO_2Me$ | Me | H | $^1$H-NMR (600.1 MHz, $CD_3CN$): 7.673 (2.0); 7.659 (2.1); 7.298 (1.7); 7.285 (1.6); 4.093 (8.5); 3.043 (16.0); 2.628 (12.0); 2.615 (12.0); 2.135 (28.1); 2.103 (0.4); 2.101 (0.5); 1.956 (0.4); 1.951 (0.7); 1.948 (3.0); 1.944 (5.3); 1.939 (7.4); 1.935 (5.1); 1.931 (2.6); 0.000 (2.7) |
| 1-451 | Me | SMe | Me | H | |
| 1-452 | Me | SEt | OMe | H | $^1$H-NMR (400.1 MHz, $CDCl_3$): 7.579 (2.4); 7.558 (2.5); 7.260 (34.2); 6.694 (2.0); 6.672 (1.9); 4.027 (9.7); 3.876 (16.0); 2.720 (1.4); 2.701 (4.4); 2.683 (4.5); 2.665 (1.5); 2.549 (13.8); 1.546 (6.4); 1.256 (1.0); 1.042 (4.7); 1.023 (9.8); 1.005 (4.5) |
| 1-453 | Me | $CO_2Et$ | SMe | H | 7.86 (d, 2H), 7.24 (d, 2H), 4.32 (q, 4H), 4.16 (s, 3H), 2.49 (s, 6H), 2.25 (s, 6H), 1.31 (t, 6H) |

TABLE 1-continued
Inventive compounds of the formula (I) in which Q is Q1, W is C—Y, R is substituted phenyl and R⁶ is methyl.
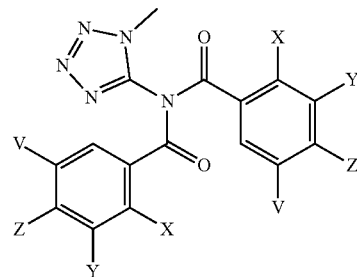
| No. | X | Y | Z | V | Physical data (¹H-NMR, DMSO-d₆, 400 MHz) |
|---|---|---|---|---|---|
| 1-454 | Me | SMe | NMe₂ | H | ¹H-NMR (400.1 MHz, CDCl₃): 7.447 (1.3); 7.426 (1.4); 7.262 (8.6); 6.766 (0.7); 6.744 (0.7); 5.298 (0.7); 4.024 (6.4); 2.852 (16.0); 2.517 (7.5); 2.131 (12.3) |
| 1-455 | Me | SMe | c-Pr | H | 7.38 (d, 2H), 6.60 (d, 2H), 4.04 (s, 3H), 2.75-2.65 (m, 2H), 2.53 (s, 6H), 2.14 (s, 6H), 1.11-1.06 (m, 4H), 0.70-0.67 (m, 4H) |
| 1-456 | Me | SMe | OMe | H | ¹H-NMR (400.1 MHz, CDCl₃): 7.548 (1.6); 7.526 (1.7); 7.262 (11.5); 6.699 (1.3); 6.678 (1.2); 4.029 (7.8); 3.903 (11.1); 2.542 (9.1); 2.203 (16.0) |
| 1-457 | Me | SMe | OEt | H | ¹H-NMR (400.1 MHz, CDCl₃): 7.506 (1.6); 7.484 (1.7); 7.266 (0.4); 7.2654 (0.5); 7.2645 (0.8); 7.261 (26.5); 7.256 (0.8); 7.2554 (0.6); 7.2546 (0.5); 7.254 (0.5); 7.253 (0.4); 7.252 (0.3); 6.665 (1.3); 6.643 (1.3); 5.299 (2.2); 4.132 (0.8); 4.124 (0.4); 4.114 (2.6); 4.108 (0.5); 4.097 (2.6); 4.079 (0.9); 4.033 (0.5); 4.027 (7.5); 3.995 (0.8); 3.788 (1.0); 2.838 (0.4); 2.511 (9.3); 2.494 (0.5); 2.322 (0.9); 2.245 (1.4); 2.240 (0.4); 2.229 (0.7); 2.228 (0.7); 2.223 (16.0); 2.193 (1.5); 2.153 (0.4); 1.526 (0.4); 1.518 (0.4); 1.509 (0.9); 1.503 (2.9); 1.494 (1.1); 1.485 (6.1); 1.477 (0.7); 1.468 (2.8); 1.258 (0.5); 1.256 (0.5); 0.000 |
| 1-458 | Me | SMe | OCH₂CF₃ | H | ¹H-NMR (400.0 MHz, d₆-DMSO): 7.789 (1.8); 7.767 (1.9); 7.030 (1.4); 7.008 (1.3); 4.901 (0.6); 4.880 (1.7); 4.858 (1.8); 4.836 (0.6); 4.145 (7.6); 3.321 (125.9); 3.297 (4.7); 2.706 (1.1); 2.524 (0.7); 2.519 (1.0); 2.510 (14.8); 2.506 (32.2); 2.501 (45.2); 2.497 (31.5); 2.492 (13.9); 2.427 (9.2); 2.279 (2.2); 2.169 (16.0); 0.858 (0.5); 0.000 (5.0) |
| 1-459 | Me | F | SMe | H | |
| 1-460 | Me | SMe | H | Me | ¹H-NMR (400.1 MHz, CDCl₃): 7.525 (0.4); 7.517 (1.5); 7.309 (1.3); 7.273 (0.6); 7.272 (0.6); 7.271 (0.7); 7.258 (264.8); 7.251 (2.7); 7.250 (2.5); 7.249 (2.2); 7.2474 (1.7); 7.2466 (1.6); 7.246 (1.4); 7.245 (1.3); 7.244 (1.1); 7.2433 (1.1); 7.2425 (1.0); 7.242 (0.9); 7.241 (0.9); 7.240 (0.8); 7.2393 (0.7); 7.2385 (0.7); 7.238 (0.6); 7.237 (0.6); 7.235 (0.5); 7.234 (0.5); 7.233 (0.4); |

TABLE 1-continued

Inventive compounds of the formula (I) in which Q is Q1, W is C—Y, R is substituted phenyl and R⁶ is methyl.

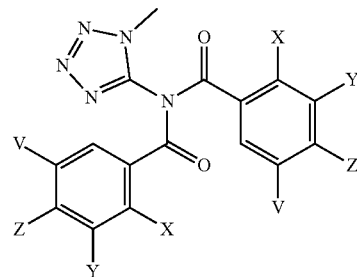

| No. | X | Y | Z | V | Physical data (¹H-NMR, DMSO-d₆, 400 MHz) |
|---|---|---|---|---|---|
| | | | | | 7.232 (0.4); 7.229 (0.4); 7.177 (0.5); 7.024 (1.7); 6.994 (1.5); 6.945 (1.7); 4.072 (10.7); 2.574 (2.3); 2.462 (4.6); 2.372 (16.0); 2.359 (2.4); 2.358 (2.4); 2.305 (7.5); 2.304 (7.8); 2.155 (8.8); 1.529 (3.4); 1.258 (1.2); 0.051 (0.4); 0.011 (0.5); 0.008 (2.7); 0.000 (86.3) |
| 1-461 | Me | NO₂ | H | Br | |
| 1-462 | Et | SMe | Br | H | |
| 1-463 | Et | SEt | Cl | H | |
| 1-464 | Et | SOMe | CF₃ | H | |
| 1-465 | Et | SOMe | Cl | H | |
| 1-466 | Et | SEt | CF₃ | H | |
| 1-467 | Et | SOEt | CF₃ | H | |
| 1-468 | Et | SO₂Et | CF₃ | H | |
| 1-469 | OMe | CH₂OMe | Cl | H | |
| 1-470 | OMe | CH₂-2H-tetrazol-2-yl | Cl | H | 8.50 (s, 2H), 7.59 (d, 2H), 7.30 (d, 2H), 6.06 (s, 2H), 4.02 (s, 3H), 3.93 (s, 6H) |
| 1-471 | OEt | SMe | CF₃ | H | ¹H-NMR (400.0 MHz, CDCl₃): 7.616 (1.1); 7.615 (1.1); 7.595 (2.3); 7.559 (3.3); 7.539 (1.6); 7.260 (21.7); 5.298 (1.1); 4.267 (1.1); 4.249 (3.5); 4.231 (3.6); 4.214 (1.1); 4.119 (11.8); 2.307 (16.0); 1.495 (4.7); 1.477 (10.2); 1.459 (4.5); 0.000 (7.1) |
| 1-472 | OEt | SO₂Me | CF₃ | H | ¹H-NMR (400.0 MHz, CDCl₃): 7.897 (0.6); 7.876 (4.3); 7.870 (5.5); 7.849 (0.8); 7.520 (0.6); 7.294 (0.6); 7.268 (0.7); 7.266 (1.1); 7.261 (109.0); 6.997 (0.6); 4.237 (0.9); 4.220 (2.8); 4.202 (2.9); 4.185 (0.9); 4.154 (13.5); 3.191 (16.0); 1.566 (4.3); 1.548 (13.4); 1.531 (4.4); 4.284 (0.8); 1.259 (1.8); 0.880 (0.7); 0.008 (1.5); 0.000 (48.2); 0.009 (1.3) |
| 1-473 | Cl | S-nPr | CF₃ | H | |
| 1-474 | Cl | SOEt | CF₃ | H | |
| 1-475 | Cl | SO₂Et | CF₃ | H | |
| 1-476 | Cl | Vinyl | SMe | H | |
| 1-477 | Cl | CH₂OMe | OMe | H | ¹H-NMR (400.0 MHz, CDCl₃): 7.596 (2.2); 7.574 (2.3); 7.260 (50.1); 6.811 (1.7); 6.789 (1.7); 4.557 (6.1); 4.060 (7.2); 3.868 (11.6); 3.325 (16.0); 1.537 (1.9); 1.256 (0.5); 0.008 (0.6); 0.000 (18.8); −0.009 (0.6) |
| 1-478 | Cl | CH₂OMe | SMe | H | |
| 1-479 | Cl | C(O)-c-Pr | Me | H | 7.47 (d, 2H), 7.17 (d, 2H), 4.09 (s, 3H), 2.26 (s, 6H), 2.12-2.07 (m, 2H), 1.32-1.29 (m, 4H), 1.15-1.10 (m, 4H) |
| 1-480 | Cl | CH(OMe)-i-Pr | Cl | H | |
| 1-481 | Cl | CH₂O—N=CH₂ | Cl | H | |
| 1-482 | Cl | CH₂O—N=CHMe | Cl | H | |
| 1-483 | Cl | CH₂O—N=CMe₂ | Cl | H | |

TABLE 1-continued

Inventive compounds of the formula (I) in which Q is Q1, W is C—Y, R is substituted phenyl and $R^6$ is methyl.

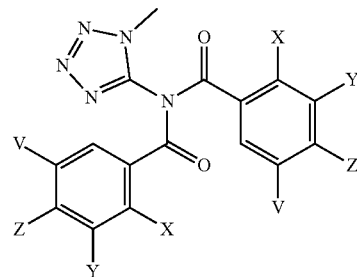

| No. | X | Y | Z | V | Physical data ($^1$H-NMR, DMSO-$d_6$, 400 MHz) |
|---|---|---|---|---|---|
| 1-484 | Cl | [diethyl(oxido)-lambda$^6$-sulfanylidene]amino | Cl | H | |
| 1-485 | Cl | (4-oxido-1,4lambda$^4$-oxathian-4-ylidene)amino | Cl | H | |
| 1-486 | Cl | 2-methylpyridin-3-yl | Me | H | |
| 1-487 | Cl | 3-methyl-4,5-dihydro-1,2-oxazol-5-yl | SMe | H | $^1$H-NMR (400.0 MHz, CDCl$_3$): 7.519 (2.0); 7.460 (1.8); 7.451 (1.9); 7.440 (2.8); 7.430 (2.7); 7.368 (2.1); 7.344 (2.4); 7.323 (1.6); 7.310 (0.7); 7.294 (3.5); 7.260 (390.8); 7.229 (0.6); 6.996 (2.1); 6.503 (0.8); 6.492 (0.8); 6.474 (1.7); 6.462 (1.6); 6.445 (0.8); 6.433 (0.8); 4.169 (7.9); 4.161 (7.9); 4.131 (0.7); 4.113 (0.6); 3.259 (2.4); 3.232 (2.1); 2.349 (15.7); 2.344 (15.3); 2.091 (16.0); 2.045 (2.5); 2.007 (2.1); 1.544 (10.2); 1.277 (0.7); 1.259 (1.6); 1.241 (0.8); 0.034 (1.2); 0.008 (3.9); 0.000 (123.9); −0.009 (3.5) |
| 1-488 | Cl | SEt | CF$_3$ | H | |
| 1-489 | Cl | Me | F | Me | 7.55 (d, 2H), 4.18 (s, 3H), 2.20 (d, 6H), 2.16 (d, 6H) |
| 1-490 | Cl | H | F | Me | $^1$H-NMR (400.0 MHz, CDCl$_3$): 7.519 (2.0); 7.460 (1.8); 7.451 (1.9); 7.440 (2.8); 7.430 (2.7); 7.368 (2.1); 7.344 (2.4); 7.323 (1.6); 7.310 (0.7); 7.294 (3.5); 7.260 (390.8); 7.229 (0.6); 6.996 (2.1); 6.503 (0.8); 6.492 (0.8); 6.474 (1.7); 6.462 (1.6); 6.445 (0.8); 6.433 (0.8); 4.169 (7.9); 4.161 (7.9); 4.131 (0.7); 4.113 (0.6); 3.259 (2.4); 3.232 (2.1); 2.349 (15.7); 2.344 (15.3); 2.091 (16.0); 2.045 (2.5); 2.007 (2.1); 1.544 (10.2); 1.277 (0.7); 1.259 (1.6); 1.241 (0.8); 0.034 (1.2); 0.008 (3.9); 0.000 (123.9); −0.009 (3.5) |
| 1-491 | Br | CH$_2$OMe | SO$_2$Me | H | |
| 1-492 | Br | F | CF$_3$ | H | |
| 1-493 | Br | 1H-pyazol-1-yl | Cl | H | |
| 1-494 | I | SMe | H | Me | |
| 1-495 | CH$_2$OMe | SMe | CF$_3$ | H | |
| 1-496 | CH$_2$OMe | SCH$_2$CH$_2$OMe | CF$_3$ | H | |
| 1-497 | c-Pr | SOMe | CF$_3$ | H | |
| 1-498 | c-Pr | SMe | Et | H | $^1$H NMR (400 MHz, CDCl$_3$): 7.260 (29.5); 7.230 (1.1); 7.210 (1.5); 7.104 (1.4); 7.084 (1.1); 4.025 (7.7); 2.960 (0.7); 2.941 (2.1); 2.922 (2.2); 2.904 (0.7); 2.322 (16.0); 2.149 (0.6); 1.535 (1.0); 1.398 (0.7); 1.224 (3.2); 1.206 (7.2); 1.187 (3.1); 1.158 (1.1); 1.154 (1.2); 1.143 (0.5); |

TABLE 1-continued

Inventive compounds of the formula (I) in which Q is Q1, W is C—Y, R is substituted phenyl and R⁶ is methyl.

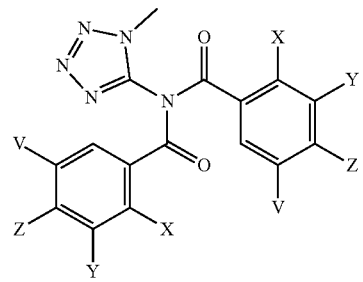

| No. | X | Y | Z | V | Physical data ($^1$H-NMR, DMSO-$d_6$, 400 MHz) |
|---|---|---|---|---|---|
|  |  |  |  |  | 1.137 (1.1); 1.133 (1.1); 0.949 (1.0); 0.945 (1.3); 0.934 (1.1); 0.000 (12.8) |
| 1-499 | SMe | vinyl | Cl | H |  |
| 1-500 | SMe | 3-methyl-4,5-dihydro-1,2-oxazol-5-yl | Cl | H |  |
| 1-501 | SO$_2$Me | 1H-pyrazol-1-yl | Cl | H | 8.63-8.38 (broad; 2H); 8.27 (s, broad, 2H), 8.09 (s broad, 2H), 7.89 (s broad, 2H), 6.58 (s broad, 2H), 4.17 (s, 3H), 3.31 (s, 6H); |
| 1-502 | SO$_2$Me | 1H-pyrazol-1-yl | CF$_3$ | H | 8.31-7.96 (broad; 4H); 7.88-7.65 (broad, 4H), 6.55 (s broad, 2H), 4.23 (s, 3H), 3.27 (s, 6H); |
| 1-503 | SO$_2$Me | 1H-pyrazol-1-yl | OMe | H | 8.49-7.89 (broad; 4H); 7.85-7.39 (broad, 4H), 6.55 (s, 2H), 4.15 (s, 3H), 3.84 (s, 6H); 3.29 (s, 6H). |
| 1-504 | SO$_2$Me | 1H-pyrazol-1-yl | Me | H | 8.09-7.73 (m; 8H); 6.58 (s, 2H), 4.16 (s, 3H), 3.31 (s, 6H); 3.08 (s, 6H). |
| 1-505 | SO$_2$Me | 1H-pyrazol-1-yl | 1H-pyrazol-1-yl | H |  |

TABLE 2

Inventive compounds of the formula (I) in which Q is Q1, W is C—Y, R is substituted phenyl and R⁶ is ethyl. Table 2 contains 454 compounds (2-1 to 2-454) in which X, Y and Z are as defined in examples 1-1 to 1-454 of table 1, and examples cited hereinafter:

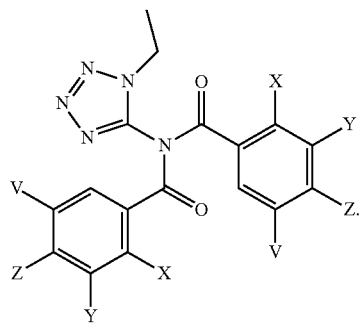

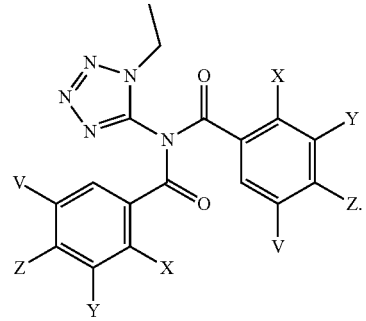

| No. | X | Y | Z | V | Physical data ($^1$H-NMR, DMSO-$d_6$, 400 MHz) |
|---|---|---|---|---|---|
| 2-460 | Me | SMe | H | Me | 7.02 (s, 2H), 6.93 (s, 2H), 4.33 (q, 2H), 2.35 (s, 6H), 2.30 (s, 6H), 2.14 (s, 6H), 1.68 (t, 3H) |
| 2-461 | Me | NO$_2$ | H | Br | $^1$H-NMR (400.0 MHz, CDCl$_3$): 8.292 (2.4); 8.287 (2.5); 8.106 (0.6); 8.101 (0.7); 8.039 (0.6); 8.034 (0.5); 8.017 (2.4); 8.012 (2.2); 7.259 (72.2); 4.553 |

TABLE 2-continued

Inventive compounds of the formula (I) in which Q is Q1, W is C—Y, R is substituted phenyl and $R^6$ is ethyl. Table 2 contains 454 compounds (2-1 to 2-454) in which X, Y and Z are as defined in examples 1-1 to 1-454 of table 1, and examples cited hereinafter:

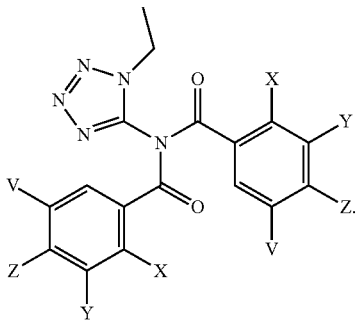

| No. | X | Y | Z | V | Physical data ($^1$H-NMR, DMSO-d$_6$, 400 MHz) |
|---|---|---|---|---|---|
| 2-463 | Et | SEt | Cl | H | (1.0); 4.535 (1.0); 3.501 (0.8); 2.610 (16.0); 2.576 (5.0); 1.684 (1.5); 1.666 (3.2); 1.647 (1.5); 0.008 (0.8); 0.000 (26.9); −0.009 (0.8) $^1$H-NMR (400.0 MHz, CDCl$_3$): 7.393 (3.5); 7.372 (6.0); 7.317 (6.6); 7.296 (3.9); 7.260 (81.7); 4.309 (1.1); 4.291 (3.5); 4.273 (3.6); 4.254 (1.1); 2.988 (1.1); 2.969 (3.6); 2.951 (3.7); 2.932 (1.2); 2.830 (2.1); 2.811 (7.1); 2793 (7.2); 2.774 (2.3); 2.044 (0.5); 1.689 (3.7); 1.671 (8.1); 1.653 (3.6); 1.551 (1.3); 1.259 (0.8); 1.256 (0.8); 1.234 (4.6); 1.216 (11.1); 1.197 (5.4); 1.195 (8.9); 1.176 (16.0); 1.158 (7.3); 0.008 (0.8); 0.000 (26.8); −0.009 (0.9) |
| 2-477 | Cl | CH$_2$OMe | OMe | H | $^1$H-NMR (400.0 MHz, CDCl$_3$): 7.607 (2.1); 7.586 (2.3); 7.260 (91.8); 6.996 (0.5); 6.799 (1.6); 6.777 (1.6); 5.298 (0.7); 4.552 (5.7); 4.342 (1.5); 4.323 (1.5); 3.863 (11.0); 3.322 (16.0); 2.101 (2.1); 1.649 (1.6); 1.631 (3.5); 1.613 (1.6); 1.536 (1.5); 1.256 (0.8); 0.008 (1.1); 0.000 (35.0); −0.009 (1.0) |
| 2-480 | Cl | CH(OMe)-i-Pr | Cl | H | $^1$H-NMR (400.0 MHz, CDCl$_3$): 7.519 (1.0); 7.409 (3.1); 7.389 (9.0); 7.367 (5.5); 7.346 (2.0); 7.260 (190.6); 7.253 (0.8); 6.996 (1.0); 4.594 (1.3); 4.348 (1.4); 4.331 (1.4); 3.137 (6.9); 2.495 (0.6); 2.005 (0.5); 1.690 (7.1); 1.671 (15.7); 1.653 (7.1); 1.256 (0.8); 1.149 (16.0); 1.132 (15.5); 0.655 (5.0); 0.639 (5.2); 0.008 (2.3); 0.007 (0.8); 0.006 (0.9); 0.005 (1.0); 0.004 (1.4); 0.000 (66.8); −0.005 (0.7); −0.006 (0.5); −0.008 (1.7) |

TABLE 2-continued

Inventive compounds of the formula (I) in which Q is Q1, W is C—Y, R is substituted phenyl and $R^6$ is ethyl. Table 2 contains 454 compounds (2-1 to 2-454) in which X, Y and Z are as defined in examples 1-1 to 1-454 of table 1, and examples cited hereinafter:

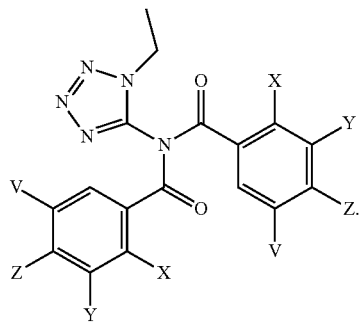

| No. | X | Y | Z | V | Physical data ($^1$H-NMR, DMSO-d$_6$, 400 MHz) |
|---|---|---|---|---|---|
| 2-499 | 2-SMe | vinyl | Cl | H | $^1$H-NMR (400.0 MHz, CDCl$_3$): 7.402 (1.7); 7.381 (2.3); 7.266 (2.0); 7.260 (17.6); 7.246 (1.4); 6.846 (0.8); 6.815 (0.6); 6.803 (0.6); 6.772 (0.9); 5.754 (5.2); 5.727 (1.4); 5.724 (1.8); 5.711 (1.7); 5.708 (1.3); 4.519 (0.5); 4.500 (1.7); 4.482 (1.7); 4.464 (0.5); 2.274 (16.0); 1.672 (1.8); 1.654 (4.0); 1.636 (1.8); 1.542 (1.6); 0.0000 (6.1) |
| 2-500 | 2-SMe | 3-methyl-4,5-dihydro-1,2-oxazol-5-yl | Cl | H | $^1$H-NMR (400.0 MHz, CDCl$_3$): 7.445 (1.7); 7.434 (1.9); 7.425 (2.7); 7.413 (2.7); 7.361 (1.7); 7.340 (1.2); 7.334 (1.8); 7.313 (1.3); 7.261 (76.7); 7.228 (0.7); 6.504 (0.8); 6.488 (0.8); 6.475 (1.7); 6.459 (1.5); 6.446 (0.8); 6.430 (0.8); 4.484 (1.1); 4.470 (1.7); 4.466 (1.3); 4.451 (1.6); 3.260 (2.1); 3.258 (2.1); 3.235 (1.7); 3.227 (1.9); 2.342 (15.5); 2.336 (14.9); 2.092 (16.0); 2.045 (0.8); 1.674 (1.9); 1.670 (2.0); 1.656 (4.4); 1.652 (4.4); 1.637 (2.0); 1.633 (2.0); 1.259 (0.6); 0.008 (0.7); 0.000 (22.1); −0.009 (0.6) |

TABLE 3

Inventive compounds of the formula (I) in which Q is Q2, W is C—Y, R is substituted phenyl and $R^7$ is methyl. Table 3 contains 454 compounds (3-1 to 3-454) in which X, Y and Z are as defined in examples 1-1 to 1-454 of table 1, and examples cited hereinafter:

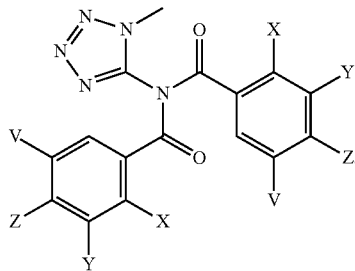

| No. | X | Y | Z | V | Physical data ($^1$H-NMR, DMSO-$d_6$, 400 MHz) |
|---|---|---|---|---|---|
| 3-95 | Me | F | SMe | H | 7.95 (s, 1H), 7.63 (d, 2H), 7.19 (dd, 2H), 3.86 (s, 3H), 2.50 (s, 6H), 2.24 (d, 6H) |
| 3-143 | Me | SMe | CF$_3$ | H | 7.99 (s, 1H), 7.94 (d, 2H), 7.71 (d, 2H), 3.95 (s, 3H), 2.64 (s, 6H), 2.22 (d, 6H) |
| 3-146 | Me | SEt | CF$_3$ | H | $^1$H-NMR (400.1 MHz, CDCl$_3$): 7.757 (4.6); 7.602 (1.7); 7.582 (2.5); 7.520 (0.4); 7.489 (2.2); 7.469 (1.6); 7.272 (0.3); 7.271 (0.4); 7.270 (0.5); 7.269 (0.7); 7.2683 (0.8); 7.2675 (1.0); 7.267 (1.2); 7.261 (75.4); 7.2534 (0.8); 7.2526 (0.7); 7.252 (0.7); 7.251 (0.6); 7.250 (0.5); 7.249 (0.5); 7.248 (0.4); 7.247 (0.4); 7.246 (0.3); 6.998 (0.4); 3.868 (13.3); 2.899 (1.4); 2.757 (0.4); 2.738 (16.0); 2.716 (1.3); 2.697 (3.7); 2.679 (3.8); 2.660 (1.3); 1.561 (1.0: 1.233 (0.5); 1.215 (1.0); 1.201 (5.0); 1.182 (10.3); 1.164 (4.8); 0.008 (0.8); 0.006 (0.4); 0.005 (0.5); 0.004 (0.7) |
| 3-202 | Et | SMe | CF$_3$ | H | |
| 3-470 | OMe | CH$_2$-2H-tetrazol-2-yl | Cl | H | 8.49 (s, 2H), 7.76 (s, 1H), 7.58 (d, 2H), 7.28 (d, 2H), 5.91 (s, 2H), 3.93 (s, 6H), 3.79 (s, 3H) |
| 3-475 | Cl | SO$_2$Et | CF$_3$ | H | $^1$H-NMR (400.0 MHz, CDCl$_3$): 7.985 (2.4); 7.964 (3.0); 7.797 (2.2); 7.776 (1.9); 7.744 (5.8); 7.267 (0.8); 7.261 (71.7); 4.148 (0.6); 4.131 (1.7); 4.113 (1.7); 4.095 (0.6); 3.940 (16.0); 3.923 (0.7); 3.867 (0.7); 3.835 (0.6); 3.500 (1.7); 3.481 (5.6); 3.462 (5.7); 3.444 (1.8); 2.097 (0.6); 2.045 (8.1); 1.455 (0.5); 1.450 (0.5); 1.438 (5.8); 1.419 (12.6); 1.401 (5.5); 1.277 (2.6); 1.266 (1.0); 1.259 (5.3); 1.241 (2.4); 0.882 (1.7); 0.864 (0.6); 0.008 (1.0); 0.000 (30.6); −0.009 (0.9) |
| 3.476 | Cl | vinyl | SMe | H | $^1$H-NMR (400.0 MHz, CDCl$_3$): 7.876 (3.7); 7.434 (2.2); 7.433 (2.2); 7.413 (2.3); 7.412 (2.4); 7.261 (24.0); 6.999 (2.4); 6.978 (2.2); 6.519 (1.1); 6.490 (1.2); 6.474 (1.2); 6.446 (1.3); 5.737 (2.4); 5.734 (2.5); |

TABLE 3-continued

Inventive compounds of the formula (I) in which Q is Q2, W is C—Y, R is substituted phenyl and R⁷ is methyl. Table 3 contains 454 compounds (3-1 to 3-454) in which X, Y and Z are as defined in examples 1-1 to 1-454 of table 1, and examples cited hereinafter:

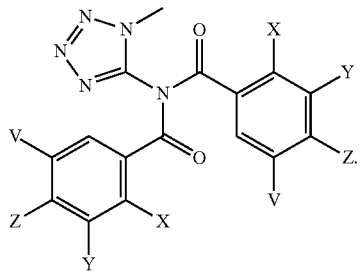

| No. | X | Y | Z | V | Physical data (¹H-NMR, DMSO-d₆, 400 MHz) |
|---|---|---|---|---|---|
| | | | | | 5.708 (2.3); 5.705 (2.4); 5.564 (2.5); 5.561 (2.4); 5.519 (2.3); 5.516 (2.2); 3.908 (12.0); 2.416 (16.0); 1.255 (0.8); 0.000 (7.3) |
| 3-477 | Cl | CH₂OMe | OMe | H | ¹H-NMR (400.0 MHz, CDCl₃): 7.804 (2.4); 7.602 (2.0); 7.581 (2.1); 7.268 (0.5); 7.2674 (0.6); 7.2666 (0.7); 7.266 (0.8); 7.265 (1.0); 7.259 (75.8); 7.255 (0.8); 7.254 (0.5); 6.802 (1.4); 6.780 (1.4); 5.298 (0.9); 4.576 (5.0); 3.873 (6.8); 3.865 (10.0); 3.325 (16.0); 1.536 (7.0); 0.008 (0.9); 0.000 (30.4); −0.009 (0.9) |
| 3-479 | Cl | C(O)-c-Pr | Me | H | 7.84 (s, 1H), 7.47 (d, 2H), 7.15 (d, 2H), 3.89 (s, 3H), 3.25 (s, 6H), 2.14-2.10 (m, 2H), 1.32-1.28 (m, 4H), 1.14-1.09 (m, 4H) |
| 3-480 | Cl | CH(OMe)-i-Pr | Cl | H | Example 3-480: ¹H-NMR (400.0 MHz, CDCl₃): 7.689 (4.9); 7.519 (0.7); 7.385 (1.6); 7.365 (3.9); 7.350 (0.6); 7.340 (4.9); 7.319 (2.0); 7.260 (127.0); 6.996 (0.7); 4.634 (1.0); 4.612 (1.1); 3.905 (7.4); 3.154 (13.8); 2.534 (0.6); 1.154 (16.0); 1.138 (15.6); 0.659 (3.7); 0.646 (3.9); 0.008 (1.3); 0.000 (44.3); −0.009 (1.3) |
| 3-486 | Cl | 2-methylpyridin-3-yl | Me | H | Example 3-486; ¹H-NMR (400.0 MHz, CDCl₃): 8.606 (1.7); 8.593 (1.7); 7.764 (3.7); 7.756 (3.3); 7.519 (0.9); 7.514 (2.2); 7.509 (1.8); 7.494 (2.6); 7.489 (2.2); 7.350 (1.4); 7.334 (1.9); 7.300 (1.9); 7.311 (0.6); 7.284 (3.4); 7.274 (2.3); 7.261 (125.8); 7.244 (1.1); 6.997 (0.7); 3.939 (2.5); 3.908 (1.1); 3.873 (14.3); 2.320 (1.4); 2.298 (1.8); 2.271 (0.6); 2.218 (7.8); 2.206 (8.0); 2.140 (0.6); 2.089 (0.5); 2.061 (1.1); 2.038 (1.9); 2.032 (1.6); 2.013 (16.0); 0.008 (1.6); 0.000 (45.1); −0.009 (1.1) |
| 3-487 | Cl | 3-methyl-4,5-dihydro-1,2-oxazol-5-yl | SMe | H | ¹H-NMR (400.0 MHz, CDCl₃): 7.926 (3.8); 7.912 (3.8); 7.522 (0.6); 7.463 (3.0); |

TABLE 3-continued

Inventive compounds of the formula (I) in which Q is Q2, W is C—Y, R is substituted phenyl and $R^7$ is methyl. Table 3 contains 454 compounds (3-1 to 3-454) in which X, Y and Z are as defined in examples 1-1 to 1-454 of table 1, and examples cited hereinafter:

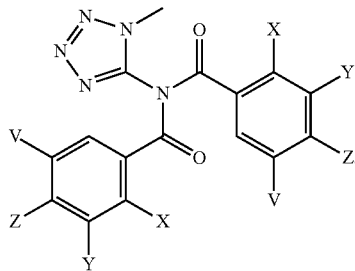

| No. | X | Y | Z | V | Physical data ($^1$H-NMR, DMSO-$d_6$, 400 MHz) |
|---|---|---|---|---|---|
| | | | | | 7.453 (2.9); 7.442 (3.5); 7.433 (3.2); 7.273 (0.5); 7.272 (0.6); 7.269 (1.0); 7.263 (115.7); 7.104 (3.5); 7.083 (3.1); 6.999 (0.6); 6.152 (1.0); 6.141 (1.0); 6.123 (2.4); 6.112 (2.5); 6.093 (1.0); 6.082 (1.0); 4.131 (0.8); 4.113 (0.8); 3.954 (1.0); 3.928 (0.6); 3.922 (10.8); 3.919 (10.7); 3.910 (0.5); 3.181 (0.9); 3.178 (1.0); 3.172 (1.1); 3.170 (1.1); 3.162 (1.1); 3.160 (1.1); 3.149 (1.8); 3.143 (1.2); 3.140 (1.1); 3.132 (1.1); 3.130 (1.0); 3.121 (1.0); 3.119 (1.1); 2.483 (15.7); 2.481 (16.0); 2.473 (1.6); 2.468 (0.8); 2.465 (0.9); 2.348 (0.5); 2.336 (0.5); 2.094 (1.7); 2.075 (12.2); 2.072 (12.0); 2.045 (3.9); 1.583 (1.1); 1.333 (0.5); 1.284 (0.8); 1.277 (1.3); 1.259 (4.1); 1.243 (1.4); 1.241 (1.3); 1.226 (0.7); 0.880 (0.7); 0.008 (0.6); 0.000 (24.6); −0.009 (0.7) |
| 3-490 | Cl | H | F | Me | 7.99 (s, 1H), 7.72 (d, 2H), 7.47 (d, 2H), 3.90 (s, 3H), 2.23 (s, 6H) |
| 3-491 | Br | CH$_2$OMe | SO$_2$Me | H | |
| 3-492 | Br | F | CF$_3$ | H | $^1$H-NMR (400.0 MHz, CDCl$_3$): 7.775 (1.7); 7.428 (0.5); 7.2674 (0.5); 7.2666 (0.6); 7.266 (0.7); 7.265 (0.9); 7.264 (1.2); 7.260 (71.3); 7.255 (0.5); 3.957 (5.7); 1.539 (16.0); 0.008 (0.8); 0.000 (27.8); −0.009 (0.8) |
| 3-493 | Br | 1H-pyrazol-1-yl | Cl | H | 7.84 (d, 2H), 7.81 (s, 1H), 7.60 (d, 2H), 7.56 (d, 2H), 7.53 (d, 2H), 6.53 (t, 2H), 3.91 (s, 3H), |
| 3-494 | I | SMe | H | Me | $^1$H-NMR (400.1 MHz, CDCl$_3$): 7.881 (3.1); 7.518 (1.2); 7.309 (0.5); 7.2803 (0.3); 7.2795 (0.4); 7.279 (0.4); 7.278 (0.4); 7.277 (0.4); 7.2763 (0.5); 7.2755 (0.5); 7.275 (0.5); 7.274 (0.6); 7.273 (0.6); 7.272 (0.7); 7.2714 (0.8); 7.2705 (0.9); 7.270 (1.0); 7.269 (1.1); 7.268 (1.3); 7.2673 (1.4); 7.2665 (1.8); 7.266 (2.1); 7.265 (2.8); 7.264 (3.6); |

TABLE 3-continued
Inventive compounds of the formula (I) in which Q is Q2, W is C—Y, R is substituted phenyl and $R^7$ is methyl. Table 3 contains 454 compounds (3-1 to 3-454) in which X, Y and Z are as defined in examples 1-1 to 1-454 of table 1, and examples cited hereinafter:
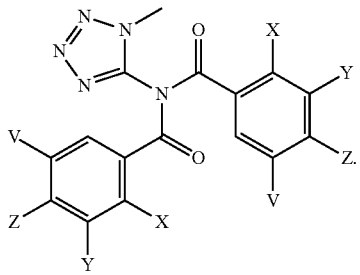
| No. | X | Y | Z | V | Physical data ($^1$H-NMR, DMSO-$d_6$, 400 MHz) |
|---|---|---|---|---|---|
| | | | | | 7.263 (4.7); 7.260 (208.2); 7.254 (4.4); 7.253 (3.7); 7.2523 (3.1); 7.2515 (2.6); 7.251 (2.2); 7.250 (2.0); 7.249 (1.6); 7.248 (1.5); 7.2474 (1.3); 7.2466 (1.2); 7.246 (1.0); 7.245 (1.0); 7.244 (0.9); 7.2433 (0.8); 7.2425 (0.7); 7.242 (0.7); 7.241 (0.6); 7.240 (0.6); 7.239 (0.5); 7.2384 (0.4); 7.2376 (0.4); 7.237 (0.4); 7.236 (0.4); 7.235 (0.4); 7.2343 (0.4); 7.2336 (0.4); 7.104 (1.7); 7.101 (1.8); 6.996 (1.2); 6.824 (1.7); 6.820 (1.7); 4.113 (0.3); 3.973 (10.2); 3.887 (0.4); 2.435 (0.4); 2.425 (0.5); 2.408 (16.0); 2.332 (11.1); 2.043 (1.6); 1.540 (91.4); 1.276 (0.6); 1.264 (0.4); 1.258 (1.1); 1.240 (0.5); 0.882 (0.7); 0.008 (1.9) |
| 3-495 | CH$_2$OMe | SMe | CF$_3$ | H | $^1$H-NMR (400.0 MHz, CDCl$_3$): 7.722 (2.6); 7.681 (1.2); 7.660 (2.0); 7.606 (1.5); 7.585 (0.9); 7.261 (24.0); 5.299 (1.1); 5.114 (5.9); 3.849 (8.0); 3.369 (16.0); 2.251 (12.5); 1.371 (1.1); 1.333 (1.2); 1.285 (2.3); 1.256 (2.9); 0.000 (9.1) |
| 3-500 | SMe | 3-methyl-4,5-dihydro-1,2-oxazol-5-1 | Cl | H | $^1$H-NMR (400.0 MHz, CDCl$_3$): 7.775 (2.6); 7.759 (2.3); 7.520 (0.5); 7.438 (1.9); 7.432 (1.7); 7.418 (3.1); 7.411 (2.5); 7.359 (2.0); 7.339 (2.4); 7.319 (1.0); 7.261 (90.4); 6.542 (0.7); 6.531 (0.8); 6.513 (1.8); 6.501 (1.5); 6.484 (0.8); 6.473 (0.8); 3.971 (7.1); 3.966 (8.5); 3.268 (2.1); 3.239 (1.9); 3.229 (1.2); 2.458 (1.0); 2.348 (12.9); 2.342 (14.9); 2.133 (0.9); 2.101 (1.1); 2.089 (16.0); 2.045 (0.7); 1.560 (1.0); 1.259 (0.8); 0.008 (0.9); 0.000 (26.7); −0.009 (0.7) |

TABLE 4

Inventive compounds of the formula (I) in which Q is Q3, W is C—Y, R is substituted phenyl and R$^8$ is methyl. Table 4 contans 454 compounds (4-1 to 4-454 ) in which X, Y and Z are as defined in examples 1-1 to 1-454 of table 1.

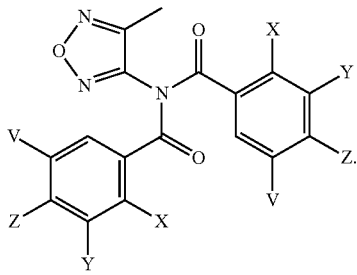

| Nr. | X | Y | Z | V | Physical data ($^1$H-NMR, DMSO-d$_6$, 400 MHz) |
|---|---|---|---|---|---|
| 4-35 | NO$_2$ | H | F | H | 8.26 (dd, 2H), 7.99 (dd, 2H), 7.88 (dd, 2H), 1.52 (s, 3H) |
| 4-36 | NO$_2$ | H | Cl | H | 8.22 (dd, 2H), 7.73 (dd, 2H), 7.49 (d, 2H), 2.48 (s, 3H) |
| 4-144 | Me | SOMe | CF$_3$ | H | 7.61 (2d, 2H), 7.49 (2d, 2H), 2.96 (s, 6H), 2.93 (s, 6H), 2.41 (s, 3H) |
| 4-157 | Me | NH$_2$ | SO$_2$Me | H | 7.45 (d, 2H), 6.98 (d, 2H), 5.99 (s, 4H), 3.10 (s, 6H), 2.45 (s, 3H), 1.99 (s, 6H) |
| 4-185 | Me | SO$_2$Me | SO$_2$Me | H | 8.37 (d, 2H), 8.18 (d, 2H), 3.56 (s, 6H), 3.51 (s, 6H), 2.69 (s, 3H) |
| 4-187 | Me | SEt | SO$_2$Me | H | $^1$H-NMR (400.1 MHz, CDCl$_3$): 8.121 (2.2); 8.101 (2.4); 7.520 (0.7); 7.518 (0.7); 7.464 (2.6); 7.443 (2.5); 7.268 (0.5); 7.267 (0.6); 7.261 (114.8); 7.259 (126.6); 7.251 (1.3); 7.250 (1.1); 7.249 (1.0); 7.2484 (0.9); 7.2476 (0.8); 7.247 (0.7); 7.246 (0.6); 7.245 (0.5); 7.2443 (0.5); 7.2435 (0.5); 7.243 (0.4); 7.242 (0.4); 7.241 (0.4); 7.240 (0.4); 7.239 (0.3); 6.997 (0.7); 6.996 (0.7); 5.298 (0.7); 3.506 (0.5); 3.486 (0.5); 3.436 (16.0); 3.047 (0.3); 2.921 (0.3); 2.911 (1.2); 2.893 (3.8); 2.874 (3.9); 2.856 (1.3); 2.739 (13.3); 2.628 (0.4); 2.433 (7.9); 2.432 (8.1); 1.532 (44.2); 1.531 (47.6); 1.312 (0.4); 1.280 (4.1); 1.261 (8.3); 1.243 (3.9); 0.010 (1.3); 0.008 (1.6); 0.001 (47.4); 0.000 (52.7) |
| 4-188 | Me | SOEt | SO$_2$Me | H | $^1$H-NMR (400.1 MHz, CDCl$_3$): 8.105 (1.8); 8.085 (2.0); 8.045 (1.3); 8.025 (1.5); 7.584 (2.3); 7.564 (2.1); 7.414 (2.3); 7.394 (2.1); 7.261 (31.7); 3.442 (16.0); 3.418 (0.8); 3.399 (0.3); 3.395 (0.4); 3.338 (12.4); 3.242 (0.7); 3.223 (0.8); 3.210 (0.6); 3.190 (0.6); 2.908 (6.3); 2.890 (1.9); 2.879 (1.7); 2.871 (1.7); 2.861 (1.6); 2.852 (0.7); 2.842 (0.5); 2.832 (0.4); 2.726 (11.6); 2.437 (15.9); 2.043 (1.3); 1.552 (10.7); 1.53 7(3.2); 1.518 (6.6); |

TABLE 4-continued

Inventive compounds of the formula (I) in which Q is Q3, W is C—Y, R is substituted phenyl and $R^8$ is methyl. Table 4 contans 454 compounds (4-1 to 4-454) in which X, Y and Z are as defined in examples 1-1 to 1-454 of table 1.

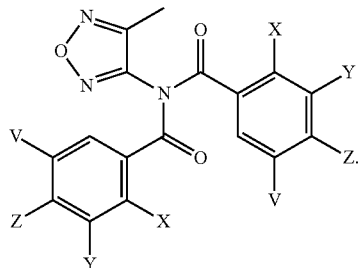

| Nr. | X | Y | Z | V | Physical data ($^1$H-NMR, DMSO-$d_6$, 400 MHz) |
|---|---|---|---|---|---|
| 4-199 | CH$_2$O(CH$_2$)$_2$OMe | NH(CH$_2$)$_3$OMe | SO$_2$Me | H | 1.499 (3.0); 1.273 (4.0); 1.254 (8.5); 1.236 (3.7); 0.008 (0.5) 7.74 (d, 2H), 7.12 (d, 2H), 4.63 (s, 4H), 3.59-3.47 (m, 12H), 3.39 (s, 6H), 3.35 (s, 6H), 3.26 (t, 4H), 3.09 (s, 6H), 2.45 (s, 3H), 1.94-1.87 (m, 4H) |
| 4-201 | Et | SO$_2$Me | Cl | H | $^1$H-NMR (400.1 MHz, CDCl$_3$): 7.494 (2.1); 7.474 (3.3); 7.406 (3.0); 7.385 (1.9); 7.262 (8.9); 5.299 (5.8); 3.352 (0.6); 3.342 (16.0); 3.263 (0.6); 3.244 (1.7); 3.226 (1.7); 3.208 (0.6); 2.413 (8.1); 2.043 (1.3); 1.550 (2.5); 1.325 (2.7); 1.307 (6.2); 1.288 (2.7); 1.276 (0.5); 1.258 (0.8); 1.240 (0.4); 0.000 (3.8) |
| 4-205 | Et | NH(CH$_2$)$_2$OMe | SO$_2$Me | H | 7.79 (d, 2H), 6.96 (d, 2H), 3.60 (t, 4H), 3.40 (s, 6H), 3.38 (t, 4H), 3.20 (s, 6H), 2.75 (q, 4H), 2.40 (s, 3H), 1.21 (t, 6H) |
| 4-358 | SMe | SMe | F | H | 7.30 (dd, 2H), 7.07 (dd, 2H), 2.50 (s, 6H), 2.48 (s, 3H), 2.39 (s, 6H) |
| 4-430 | Me | CH$_2$SMe | CF$_3$ | H | $^1$H-NMR (400.0 MHz, CDCl$_3$): 7.506 (1.6); 7.485 (2.0); 7.337 (1.8); 7.317 (1.4); 7.265 (0.6); 7.264 (0.8); 7.263 (1.0); 7.260 (45.6); 3.805 (5.7); 2.608 (0.6); 2.540 (14.0: 2.424 (14.9); 2.387 (0.6); 2.189 (0.5); 2.163 (0.8); 2.115 (16.0); 1.535 (5.3); 0.008 (0.5); 0.000 (18.7) |
| 4-448 | Me | NMe$_2$ | CF$_3$ | H | $^1$H-NMR (400.0 MHz, CDCl$_3$): 7.454 (1.0); 7.433 (1.2); 7.301 (1.1); 7.281 (0.9); 7.260 (35.3); 2.692 (16.0); 2.430 (8.0); 2.287 (8.3); 1.539 (14.4); 0.000 (12.0) |
| 4-449 | Me | NHMe | CF$_3$ | H | $^1$H-NMR (400.0 MHz, CDCl$_3$): 7.364 (2.0); 7.343 (2.2); 7.260 (43.3); 7.067 (1.9); 7.047 (1.7); 2.736 (13.1); 2.421 (14.5); 2.352 (16.0: 1.543 (0.8); 1.255 (1.0); 0.000 (14.9) |
| 4-451 | Me | SMe | Me | H | $^1$H-NMR (400.0 MHz, CDCl$_3$): 7.302 (1.4); 7.2683 (1.7); 7.260 (14.1); 7.073 (1.2); 7.053 (1.0); 2.554 (8.7); 2.497 (8.1); 2.404 (8.4); 2.243 (0.7); 2.090 (16.0); 1.546 (1.7); 1.366 (0.8); 0.000 (4.8) |

TABLE 4-continued

Inventive compounds of the formula (I) in which Q is Q3, W is C—Y, R is substituted phenyl and $R^8$ is methyl. Table 4 contans 454 compounds (4-1 to 4-454) in which X, Y and Z are as defined in examples 1-1 to 1-454 of table 1.

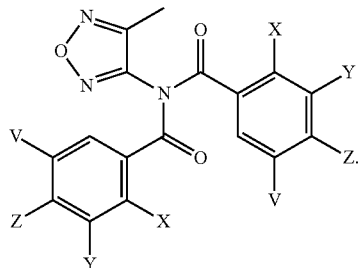

| Nr. | X | Y | Z | V | Physical data ($^1$H-NMR, DMSO-$d_6$, 400 MHz) |
|---|---|---|---|---|---|
| 4-452 | Me | SEt | OMe | H | 7.48 (d, 2H), 6.66 (d, 2H), 3.88 (s, 6H), 2.69 (q, 4H), 2.51 (s, 6H), 2.39 (s, 3H), 1.01 (t, 6H) |
| 4-457 | Me | SMe | OEt | Me | $^1$H-NMR (400.1 MHz, CDCl$_3$): 7.396 (1.7); 7.374 (1.8); 7.265 (0.4); 7.260 (16.4); 6.647 (1.3); 6.625 (1.3); 5.298 (1.1); 4.125 (0.8); 4.107 (2.5); 4.090 (2.6); 4.072 (0.8); 2.696 (0.8); 2.522 (0.4); 2.505 (0.4); 2.495 (9.4); 2.481 (1.3); 2.396 (1.5); 2.392 (7.8); 2.383 (0.4); 2.357 (1.4); 2.325 (0.5); 2.248 (0.5); 2.231 (0.7); 2.228 (0.4); 2.221 (16.0); 1.528 (0.6); 1.510 (0.4); 1.500 (2.9); 1.492 (0.5); 1.482 (6.3); 1.465 (2.8) |
| 4-460 | Me | SMe | H | Me | |
| 4-466 | Et | SEt | CF$_3$ | H | $^1$H-NMR (400.0 MHz, CDCl$_3$): 7.607 (2.9); 7.586 (3.5); 7.392 (2.4); 7.372 (2.0); 7.260 (39.8); 3.143 (1.0); 3.124 (3.5); 3.106 (3.6); 3.087 (1.1); 2.745 (1.4); 2.726 (4.5); 2.708 (4.6); 2.689 (1.5); 2.415 (16.0); 1.538 (14.0); 1.292 (4.5); 1.273 (10.9); 1.255 (4.9); 1.251 (6.6); 1.232 (12.3); 1.213 (5.6); 0.008 (0.5); 0.000 (17.2); −0.009 (0.5) |
| 4-469 | OMe | CH$_2$OMe | Cl | H | 7.42 (d, 2H), 7.35 (d, 2H), 4.38 (s, 4H), 3.92 (s, 6H), 3.40 (s, 6H), 2.42 (s, 3H) |
| 4-470 | OMe | CH$_2$-2H-tetrazol-2-yl | Cl | H | 8.49 (s, 2H), 7.53 (d, 2H), 7.26 (d, 2H), 5.85 (s, 4H), 3.93 (s, 6H), 2.39 (s, 3H) |
| 4-471 | OEt | SMe | CF$_3$ | H | 7.51 (d, 2H), 7.49 (d, 2H), 4.22 (q, 4H), 2.44 (s, 3H), 2.30 (s, 6H), 1.46 (t, 6H) |
| 4-477 | Cl | CH$_2$OMe | OMe | H | $^1$H-NMR (400.0 MHz, CDCl$_3$): 7.540 (2.1); 7.519 (2.4); 7.260 (30.9); 6.805 (1.5); 6.783 (1.4); 4.565 (5.4); 3.866 (10.5); 3.326 (16.0); 2.419 (7.1); 1.539 (1.2); 0.000 (11.9) |
| 4-481 | Cl | CH$_2$O—N=CH$_2$ | Cl | H | |
| 4-482 | Cl | CH$_2$O—N=CHMe | Cl | H | |
| 4-483 | Cl | CH$_2$O—N=CMe$_2$ | Cl | H | |
| 4-487 | Cl | 3-methyl-4,5-dihydro-1,2-oxazol-5-yl | SMe | H | $^1$H-NMR (400.0 MHz, CDCl$_3$): 7.520 (0.7); 7.414 (2.6); 7.401 (2.3); 7.393 (3.0); 7.380 (2.6); 7.273 (0.5); 7.2724 (0.5); 7.2716 (0.6); 7.271 (0.7); 7.270 (0.7); 7.269 (0.9); 7.2684 (1.1); 7.2676 (1.2); |

TABLE 4-continued
Inventive compounds of the formula (I) in which Q is Q3, W is C—Y, R is substituted phenyl and $R^8$ is methyl. Table 4 contans 454 compounds (4-1 to 4-454) in which X, Y and Z are as defined in examples 1-1 to 1-454 of table 1.
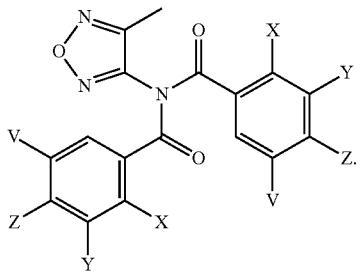
| Nr. | X | Y | Z | V | Physical data ($^1$H-NMR, DMSO-$d_6$, 400 MHz) |
|---|---|---|---|---|---|
|  |  |  |  |  | 7.267 (1.4); 7.266 (1.7); 7.265 (2.3); 7.261 (126.8); 7.083 (3.0); 7.063 (2.6); 6.997 (0.7); 6.137 (0.8); 6.129 (0.9); 6.108 (2.0); 6.099 (2.1); 6.078 (0.9); 6.070 (0.9); 4.149 (1.1); 4.131 (3.3); 4.113 (3.4); 4.095 (1.1); 3.175 (0.8); 3.166 (0.8); 3.159 (0.9); 3.146 (1.5); 3.139 (0.9); 3.137 (0.9); 3.130 (0.9); 3.128 (0.8); 3.118 (0.9); 2.485 (14.4); 2.476 (1.1); 2.472 (1.0); 2.469 (1.2); 2.443 (15.8); 2.319 (0.6); 2.095 (0.7); 2.080 (10.1); 2.077 (9.8); 2.045 (16.0); 1.548 (45.2); 1.277 (4.8); 1.259 (10.1); 1.241 (4.7); 0.008 (1.6); 0.006 (0.6); 0.005 (0.7); 0.004 (0.9); 0.000 (49.9); −0.005 (0.7); −0.009 (1.3) |
| 4-495 | CH$_2$OMe | SMe | CF$_3$ | H | $^1$H-NMR (400.1 MHz, CDCl$_3$): 7.664 (1.2); 7.644 (1.6); 7.500 (1.3); 7.480 (1.0); 7.259 (17.1); 5.017 (5.7); 3.405 (0.4); 3.392 (16.0); 3.353 (0.4); 2.593 (0.4); 2.413 (7.7); 2.270 (0.5); 2.269 (0.4); 2.255 (11.1); 2.043 (0.6); 1.569 (0.4); 1.432 (3.8); 1.258 (0.4); 0.000 (7.2) |
| 4-496 | CH$_2$OMe | SCH$_2$CH$_2$OMe | CF$_3$ | H |  |

TABLE 5

Inventive compounds of the formula (I) in which Q is Q3, W is C—Y, W is C—Y, R is substituted phenyl and $R^8$ is chlorine. Table 5 contains 454 compounds (5-1 to 5-454) in which X, Y and Z are as defined in examples 1-1 to 1-454 of table 1, and examples cited hereinafter.

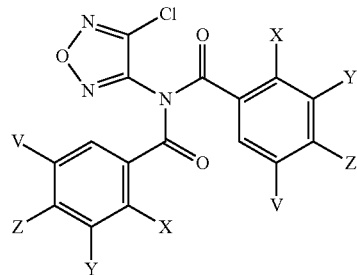

| Nr. | X | Y | Z | V | Physical data ($^1$H-NMR, DMSO-$d_6$, 400 MHz) |
|---|---|---|---|---|---|
| 5-451 | Me | SMe | Me | H | $^1$H-NMR (400.0 MHz, CDCl$_3$): 7.350 (1.3); 7.330 (1.5); 7.260 (36.4); 7.87 (1.1); 7.067 (0.9); 2.572 (8.2); 2.505 (7.6); 2.099 (16.0); 1.536 (12.0); 0.000 (13.0) |
| 5-462 | Et | SMe | Br | H | |
| 5-466 | Et | SEt | CF$_3$ | H | $^1$H-NMR (400.0 MHz, CDCl$_3$): 7.628 (3.9); 7.607 (4.8); 7.519 (2.2); 7.469 (3.8); 7.448 (2.9); 7.293 (2.3); 7.260 (412.7); 7.225 (0.8); 6.996 (2.2); 3.152 (1.7); 3.133 (4.9); 3.115 (5.1); 3.096 (1.7); 2.748 (2.1); 2.729 (6.2); 2.710 (6.4); 2.692 (2.1); 1.570 (1.0); 1.537 (164.7); 1.293 (6.9); 1.275 (15.5); 1.256 (8.3); 1.252 (9.0); 1.233 (16.0); 1.214 (7.3); 0.899 (1.4); 0.882 (3.9); 0.864 (1.6); 0.146 (0.7); 0.033 (1.0); 0.008 (8.6); 0.000 (170.3); −0.009 (4.5); −0.150 (0.7) |
| 5-477 | Cl | CH$_2$OMe | OMe | H | $^1$H-NMR (400.0 MHz, CDCl$_3$): 7.587 (2.0); 7.565 (2.2); 7.268 (0.5); 7.2673 (0.6); 7.2665 (0.7); 7.266 (0.9); 7.265 (1.0); 7.264 (1.3); 7.263 (1.6); 7.259 (89.9); 7.256 (1.8); 7.255 (1.2); 7.2543 (0.8); 7.2535 (0.6); 6.816 (1.4); 6.794 (1.3); 4.565 (5.0); 3.873 (9.8); 3.324 (16.0); 1.531 (10.7); 0.008 (1.1); 0.000 (36.7); −0.009 (1.0) |
| 5-484 | Cl | [diethyl(oxido)-lambda$^6$-sulfanylidene]amino | Cl | H | $^1$H-NMR (400.0 MHz, CDCl$_3$): 7.521 (0.6); 7.330 (20.6); 7.320 (0.6); 7.319 (0.6); 7.309 (26.0); 7.270 (0.7); 7.262 (100.4); 7.140 (24.3); 7.134 (0.5); 7.119 (20.6); 6.998 (0.6); 4.130 (1.3); 4.113 (1.3); 3.281 (0.7); 3.263 (2.2); 3.246 (5.4); 3.235 (4.9); 3.227 (15.9); 3.217 (15.5); 3.209 (16.0); 3.198 (16.0); 3.190 (5.3); 3.180 (5.7); 3.163 (2.2); 3.145 (0.7); 2.045 (6.0); 1.555 (20.5); 1.478 (43.4); 1.460 (97.5); 1.441 (41.6); 1.425 (0.7); 1.295 (0.6); 1.277 (2.1); 1.259 (4.5); 1.247 (0.5); 1.241 (1.9); 0.008 (1.4); 0.000 (48.1); −0.009 (1.3) |
| 5-485 | Cl | (4-oxido-1,4lambda$^4$-oxathian-4-ylidene)amino | Cl | H | $^1$H-NMR (400.0 MHz, CDCl$_3$): 7.713 (0.7); 7.692 (0.7); 7.529 (0.8); 7.520 (3.7); 7.508 (0.9); |

TABLE 5-continued
Inventive compounds of the formula (I) in which Q is Q3, W is C—Y, W is C—Y, R is substituted phenyl and $R^8$ is chlorine. Table 5 contains 454 compounds (5-1 to 5-454) in which X, Y and Z are as defined in examples 1-1 to 1-454 of table 1, and examples cited hereinafter.
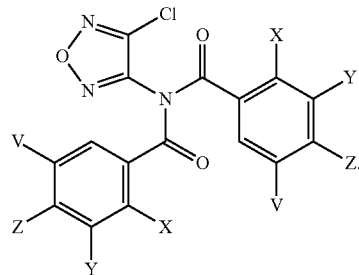
| Nr. | X | Y | Z | V | Physical data ($^1$H-NMR, DMSO-$d_6$, 400 MHz) |
|-----|---|---|---|---|---|
| | | | | | 7.492 (0.6); 7.482 (1.3); 7.420 (0.6); 7.390 (1.5); 7.369 (1.0); 7.354 (1.3); 7.349 (1.8); 7.343 (47.9); 7.333 (1.4); 7.328 (2.1); 7.322 (57.2); 7.302 (0.5); 7.298 (0.6); 7.295 (0.6); 7.291 (0.9); 7.290 (0.9); 7.289 (0.8); 7.2864 (0.9); 7.2856 (1.0); 7.285 (1.0); 7.284 (1.1); 7.283 (1.2); 7.2824 (1.3); 7.2816 (1.3); 7.281 (1.4); 7.280 (1.4); 7.279 (1.6); 7.2784 (1.7); 7.2776 (1.9); 7.277 (2.0); 7.276 (2.2); 7.2752 (2.5); 7.2745 (2.5); 7.274 (2.8); 7.273 (3.1); 7.272 (3.4); 7.271 (3.4); 7.2704 (3.8); 7.2696 (4.6); 7.269 (5.7); 7.268 (5.8); 7.2673 (6.7); 7.2665 (8.2); 7.266 (9.8); 7.265 (12.3); 7.264 (17.0); 7.261 (625.8); 7.256 (6.1); 7.255 (3.7); 7.254 (2.7); 7.2534 (2.4); 7.2526 (1.8); 7.252 (1.5); 7.251 (1.4); 7.250 (1.1); 7.2494 (0.9); 7.2486 (0.9); 7.248 (1.2); 7.247 (0.7); 7.228 (0.6); 7.211 (0.5); 7.173 (0.8); 7.160 (55.2); 7.39 (45.5); 7.126 (0.6); 6.997 (3.6); 4.328 (6.6); 4.320 (8.8); 4.314 (7.6); 4.305 (7.3); 4.297 (10.0); 4.268 (11.1); 4.282 (13.5); 4.273 (10.5); 4.193 (11.4); 4.187 (13.2); 4.172 (12.2); 4.165 (13.1); 4.155 (8.3); 4.149 (2.9); 4.140 (8.7); 4.134 (8.2); 4.113 (3.2); 4.095 (1.2); 3.492 (6.3); 3.482 (5.6); 3.471 (6.1); 3.460 (11.6); 3.450 (8.6); 3.437 (7.6); 3.429 (8.2); 3.364 (1.2); 3.360 (0.9); 3.280 (10.6); 3.272 (11.4); 3.266 (10.4); 3.251 (5.2); 3.243 (7.8); 3.237 (8.3); 3.229 (7.5); 2.045 (13.8); 1.864 (0.6); 1.545 (157.1); 1.300 (1.2); 1.,277 (5.5); 1.259 (16.0); 1.241 (5.7); 1.138 (0.7); 1.085 (0.7); 1.052 (0.6); 0.880 (3.5); 0.863 (1.9); 0.853 (2.1); 0.836 (1.5); 0.146 (0.8); 0.000 (282.3); −0.006 (4.3); 0.007 (3.6); −0.008 (8.6); 0.012 (1.7); −0.150 (0.9) |

TABLE 6

Inventive compounds of the formula (I) in which Q is Q4, W is C—Y, R is substituted phenyl and $R^9$ is methyl. Table 6 contains 454 compounds (6-1 to 6-454) in which X, Y and Z are as defined in examples 1-1 to 1-454 of table 1, and examples cited hereinafter.

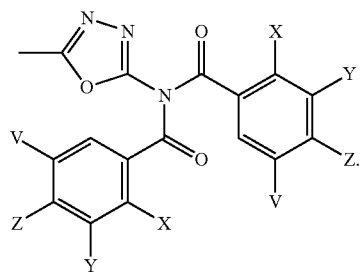

TABLE 7

Inventive compounds of the formula (I) having 2 identical acyl radicals, in which Q is Q1, W is N and $R^6$ is methyl.

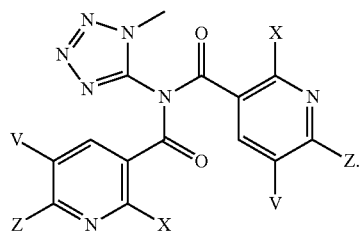

| No. | X | Z | V | Physical data ($^1$H-NMR, DMSO-$d_6$, 400 MHz) |
|---|---|---|---|---|
| 7-1 | F | $CF_3$ | H | |
| 7-2 | Cl | $CF_3$ | H | |
| 7-3 | Br | $CF_3$ | H | |
| 7-4 | Me | $CF_3$ | H | |
| 7-5 | $CH_2OMe$ | $CF_3$ | H | |
| 7-6 | $CH_2CH_2OCH_2OMe$ | $CF_3$ | H | |
| 7-7 | $CH_2$-1,2-thiazolidine 1,1-dioxide | $CF_3$ | H | |
| 7-8 | $CH_2$-pyrrolidin-2-one | $CF_3$ | H | |
| 7-9 | F | F | H | |
| 7-10 | Cl | Cl | H | |
| 7-11 | Br | Br | H | |
| 7-12 | $CF_3$ | $CF_3$ | H | |
| 7-13 | F | $SO_2Me$ | H | |
| 7-14 | Cl | $SO_2Me$ | H | |
| 7-15 | Br | $SO_2Me$ | H | |
| 7-16 | OMe | OMe | H | |

TABLE 8

Inventive compounds of the formula (I) in which Q is Q1, W is N and $R^6$ is ethyl. Table 8 contains 16 compounds (8-1 to 8-16) in which X, Y and Z are as defined in examples 7-1 to 7-16 of table 7.

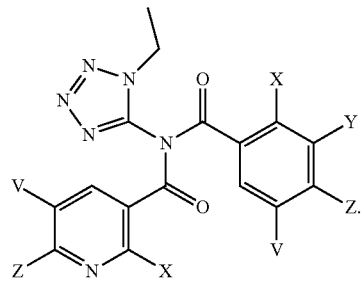

| No. | X | Z | V | Physical data ($^1$H NMR, DMSO-$d_6$, 400 MHz) |
|---|---|---|---|---|
| 8-16 | OMe | OMe | H | 7.91 (d, 2H), 6.45 (d, 2H), 4.30 (q, 2H), 3.86 (s, 6H), 3.85 (s, 6H), 1.45 (t, 3H) |

TABLE 9

Inventive compounds of the formula (I) in which Q is Q2, W is C—Y, R is substituted phenyl and $R^7$ is methyl. Table 9 contains 16 compounds (9-1 to 9-16) in which X, Y and Z are as defined in examples 7-1 to 7-16 of table 7.

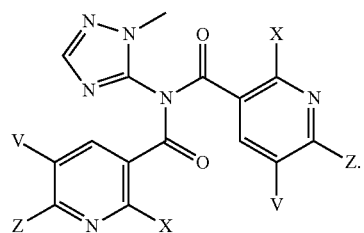

TABLE 10

Inventive compounds of the formula (I) in which Q is Q3, W is N, R is substituted phenyl and $R^8$ is methyl. Table 10 contains 16 compounds (10-1 to 10-16) in which X, Y and Z are as defined in examples 7-1 to 7-16 of table 7.

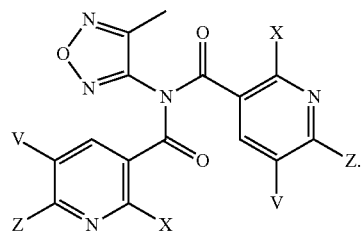

| No. | X | Z | V | Physical data ($^1$H-NMR, DMSO-$d_6$, 400 MHz) |
|---|---|---|---|---|
| 10-7 | $CH_2$-1,2-thiazolidine 1,1-dioxide | $CF_3$ | H | |

TABLE 11

Inventive compounds of the formula (I) in which Q is Q3, W is N, R is substituted phenyl and $R^8$ is chlorine. Table 11 comprises 16 compounds (11-1 to 11-16) in which X, Y and Z are defined in Table 7.

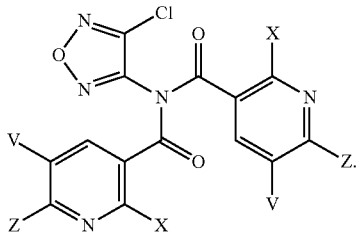

TABLE 12

Inventive compounds of the formula (I) having 2 identical acyl radicals, in which Q is Q4, W is N and $R^9$ is methyl. Table 12 comprises 16 compounds (12-1 to 12-16) in which X, Y and Z are defined in Table 7.

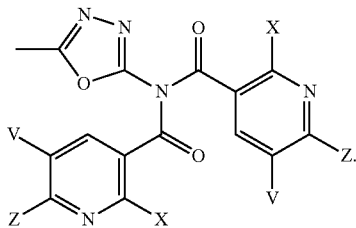

TABLE 13

Inventive compounds of the formula (I) in which Q is Q1, Z is methylsulfonyl, W is C—H, Z is trifluoromethyl, V is hydrogen and $R^6$ is methyl.

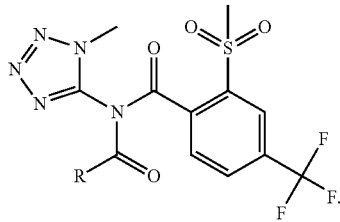

| No. | R | Physical data, ($^1$H-NMR, DMSO-$d_6$, 400 MHz) |
|---|---|---|
| 1 | Me | 8.36 (s, 1H), 8.26 (d, 1H), 8.06 (d, 1H), 4.12 (s, 3H), 3.38 (s, 3H), 2.22 (s, 3H) |
| 2 | Et | |
| 3 | i-Pr | |
| 4 | c-Pr | |
| 5 | $CH_2CHMe_2$ | |
| 6 | $CF_3$ | |
| 7 | $CH_2CHF_2$ | |
| 8 | $CH_2CF_3$ | |
| 9 | $CH_2OMe$ | |
| 10 | $CH_2SMe$ | |
| 11 | $CH_2SO_2Me$ | |
| 12 | $CH_2CN$ | |
| 13 | $CH_2CH_2OMe$ | |
| 14 | $CH_2CH_2OEt$ | |
| 15 | $CH_2CH_2OPh$ | |
| 16 | $CH_2CH_2SMe$ | |
| 17 | $CH_2CH_2S(O)Me$ | |
| 18 | $CH_2CH_2SO_2Me$ | |
| 19 | $CH_2C(O)Me$ | |
| 20 | $CH_2C(O)Ph$ | |
| 21 | $CH_2CO_2H$ | |

TABLE 13-continued

Inventive compounds of the formula (I) in which Q is Q1, Z is methylsulfonyl, W is C—H, Z is trifluoromethyl, V is hydrogen and $R^6$ is methyl.

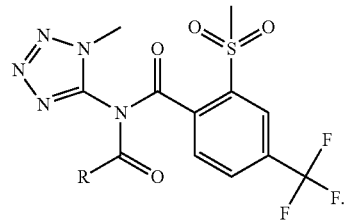

| No. | R | Physical data, ($^1$H-NMR, DMSO-$d_6$, 400 MHz) |
|---|---|---|
| 22 | $CH_2CO_2Me$ | |
| 23 | $CH_2CN$ | |
| 24 | $CH_2C(O)Me$ | |
| 25 | $CH_2CO_2H$ | |
| 26 | $CH_2CO_2Me$ | |
| 27 | $CH_2CH_2CN$ | |
| 28 | allyl | |
| 29 | propargyl | |
| 30 | phenyl | |
| 31 | 4-Cl-phenyl | 8.44 (d, 1H), 8.40 (s, 1H), 8.31 (d, 1H), 7.63 (d, 2H), 7.52 (d, 2H), 4.22 (s, 3H), 3.41 (s, 3H) |
| 32 | 4-OMe-Ph | 8.40 (d, 1H), 8.39 (s, 1H), 8.29 (d, 1H), 7.58 (d, 2H), 6.97 (d, 2H), 4.20 (s, 3H), 3.79 (s, 3H), 3.41 (s, 3H) |
| 33 | pyridin-3-yl | |
| 34 | benzyl | |

C. Biological Examples

1. Pre-Emergence Herbicidal Action Against Harmful Plants

Seeds of monocotyledonous and dicotyledonous weed plants and crop plants are laid out in sandy loam in wood-fiber pots and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). In this case, for example, compound Nos. 1-086, 1-028, 1-206, 1-447, 1-448, 1-449, 1-454, 1-458, 1-470, 1-471, 1-472, 1-477, 1-487, 2-477, 2-480, 2-500, 3-143, 3-475, 3-491, 4-188, 4-495, 4-430, 4-496, 13-001, 13-031 and 13-032, at an application rate of 320 g/ha, each show at least 80% efficacy against *Abutilon theophrasti* and *Veronica persica*.

2. Post-Emergence Herbicidal Action Against Harmful Plants

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). In this case, for example, compound Nos. 1-028, 1-085, 1-086, 1-206, 1-447, 1-448, 1-449, 1-453, 1-457, 1-460, 1-470, 1-471, 1-472, 1-487, 2-500, 3-143, 3-146, 3-487, 3-491, 3-492, 4-144, 4-188, 13-001, 13-031 and 13-032, at an application rate of 80 g/ha, each show at least 80% efficacy against *Abutilon theophrasti* and *Veronica persica*.

The invention claimed is:

1. An acylated N-(1,2,5-oxadiazol-3-yl)-, N-(1,3,4-oxadiazol-2-yl)-, N-(tetrazol-5-yl)- or N-(triazol-5-yl)arylcarboxamide, and/or a salt thereof, of formula (I)

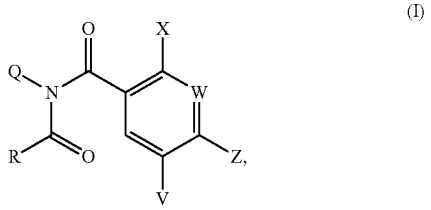

(I)

wherein the symbols and indices are defined as follows:
R is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkyl-$(C_1-C_6)$-alkyl, $(C_3-C_6)$-halocycloalkyl-$(C_1-C_6)$-alkyl, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$C(O)R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $COOR^1$, $CON(R^1)_2$, or phenyl, heteroaryl, heterocyclyl or benzyl, each substituted by s radicals selected from the group consisting of X, Y, Z and V,
W is N or CY,
X and Z are each independently hydrogen, nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR^1R^2$, $P(O)(OR^5)_2$, or
heteroaryl, heterocyclyl or phenyl, each substituted by s radicals selected from the group consisting of methyl, ethyl, methoxy, nitro, trifluoromethyl and halogen,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $CH=NOR^1$, $(C_1-C_6)$-alkyl-$CH=NOR^1$, $(C_1-C_6)$-alkyl-O—N=$C(R^1)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$-$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, or Y and Z together with the two atoms to which they are bonded form a 5-, 6- or 7-membered, unsaturated, partly saturated or saturated ring which, as well as carbon atoms, in each case comprises s nitrogen atoms, n oxygen atoms, n sulfur atoms and n S(O), $S(O)_2$, C=N—$R^{17}$, $C(OR^{17})_2$, C[—O—$(CH_2)_2$—O-] or C(O) elements as ring members,
wherein the carbon atoms are substituted by s radicals selected from the group consisting of halogen, cyano, $(C_1-C_6)$-alkyl, $(C_2-C_{10})$-alkenyl, $(C_2-C_{10})$-alkynyl, $(C_1-C_6)$-haloalkyl, $(C_1-C_6)$-alkoxy, phenoxy, halo-$(C_1-C_6)$-alkoxy, $(C_3-C_8)$-cycloalkyl, $(C_2-C_8)$-alkoxyalkyl and phenyl, wherein the nitrogen atoms are substituted by n radicals selected from the group consisting of $(C_1-C_6)$-alkyl and phenyl,
and wherein the aforementioned phenyl radicals are substituted by s radicals selected from the group consisting of cyano, nitro, halogen, $(C_1-C_6)$-alkyl, $(C_1-C_6)$-haloalkyl and $(C_1-C_6)$-alkoxy,
V is hydrogen, nitro, halogen, cyano, $(C_1-C_4)$-alkyl, $(C_1-C_4)$-haloalkyl, $OR^1$, $S(O)_nR^2$,
$R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 latter radicals are substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups,
$R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 latter radicals are substituted by s radicals selected from the group consisting of cyano, halogen, nitro, thiocyanato, $OR^3$, $S(O)_nR^4$, $N(R^3)_2$, NR³OR³, COR³, OCOR³, SCOR⁴, NR³COR³, NR³SO₂R⁴, CO₂R³, COSR⁴, CON(R³)₂ and (C₁-C₄)-alkoxy-(C₂-C₆)-alkoxycarbonyl, and where heterocyclyl bears n oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, $(C_3-C_6)$-cycloalkyl or $(C_3-C_6)$-cycloalkyl-$(C_1-C_6)$-alkyl, $R^5$ is $(C_1-C_4)$-alkyl, n is 0, 1 or 2, s is 0, 1, 2 or 3, Q is a Q1, Q2, Q3 or Q4 radical

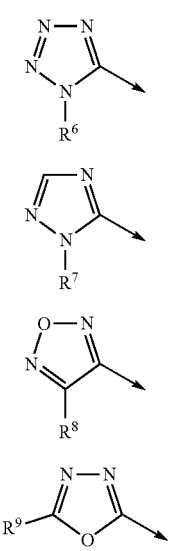

$R^6$ and $R^7$ are independently $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, or halo-$(C_2-C_6)$-alkynyl, where these 6 aforementioned radicals are each substituted by s radicals selected from the group consisting of nitro, cyano, $SiR^{12}_3$, $PO(OR^{12})_3$, $S(O)_n$-$(C_1-C_6)$-alkyl, $(C_1-C_6)$-alkoxy, halo-$(C_1-C_6)$-alkoxy, $N(R^{10})_2$, $COR^{10}$, $COOR^{10}$, $OCOR^{10}$, $OCO_2R^{10}$, $NR^{10}COR^{10}$, $NR^{10}SO_2R^{11}$, $(C_3-C_6)$-cycloalkyl, heteroaryl, heterocyclyl, phenyl, D-heteroaryl, D-heterocyclyl, D-phenyl or D-benzyl, and where the 7 latter radicals are substituted by s radicals selected from the group of methyl, ethyl, methoxy, trifluoromethyl and halogen, and where heterocyclyl bears n oxo groups, or $R^6$ and $R^7$ are each $(C_3-C_7)$-cycloalkyl, heteroaryl, heterocyclyl or phenyl, each substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$-$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^8$ is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, halo-$(C_2-C_6)$-alkenyl, $(C_2-C_6)$-alkynyl, $(C_2-C_6)$-alkynyloxy, halo-$(C_2-C_6)$-alkynyl, cyano, nitro, methylsulfenyl, methylsulfinyl, methylsulfonyl, $(C_1-C_6)$-alkylcarbonylamino, $(C_1-C_6)$-alkoxycarbonylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each substituted by s radicals selected from the group consisting of methyl, ethyl, methoxy, trifluoromethyl and halogen;

$R^9$ is hydrogen, $(C_1-C_6)$-alkyl, $R^{13}O$-$(C_1-C_6)$-alkyl, $CH_2R^{14}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^{13}$, $NHR^{13}$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$-$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{10}$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl or phenyl, $R^{11}$ is $(C_1-C_6)$-alkyl, $(C_2-C_6)$-alkenyl, $(C_2-C_6)$-alkynyl or phenyl, $R^{12}$ is $(C_1-C)$-alkyl, $R^{13}$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O-$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{15}$-heteroaryl or $(C_1-C_6)$-alkyl-$NR^{15}$-heterocyclyl, where the 21 latter radicals are substituted by s radicals selected from the group consisting of cyano, halogen, nitro, thiocyanato, $OR^{15}$, $S(O)_nR^{16}$, $N(R^{15})_2$, $NR^{15}OR^{15}$, $COR^{15}$, $OCOR^{15}$, $SCOR^{16}$, $NR^{15}COR^{15}$, $NR^{15}SO_2R^{16}$, $CO_2R^{15}$, $COSR^{16}$, $CON(R^{15})_2$ and $(C_1-C_4)$-alkoxy-$(C_2-C_6)$-alkoxycarbonyl, and where heterocyclyl bears n oxo groups, $R^{14}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_3-C_6)$-alkoxy, $(C_3-C_6)$-cycloalkyl, or heteroaryl, heterocyclyl or phenyl, each substituted by s radicals selected from the group consisting of methyl, ethyl, methoxy, trifluoromethyl and halogen;

$R^{15}$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^{16}$ is $(C_1-C_6)$-alkyl, $(C_2-C_6)$-alkenyl or $(C_2-C_6)$-alkynyl, $R^{17}$ is $(C_1-C_6)$-alkyl, halo-$(C_1-C_6)$-alkyl, $(C_1-C_6)$-alkoxy or halo-$(C_1-C_6)$-alkoxy, s is 0, 1, 2 or 3, n is 0, 1 or 2, D is O, S, or $NR^{11}$, with the proviso that V, W, X, Y and Z are not simultaneously hydrogen.

2. The acylated N-(1,2,5-oxadiazol-3-yl)-, N-(1,3,4-oxadiazol-2-yl)-, N-(tetrazol-5-yl)- or N-(triazol-5-yl)arylcarboxamide of formula (I) and/or a salt as claimed in claim 1, wherein R is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-cycloalkyl-$(C_1-C_6)$-alkyl, $(C_3-C_6)$-halocycloalkyl-$(C_1-C_6)$-alkyl, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$C(O)R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $COOR^1$, $CON(R^1)_2$, or phenyl, heteroaryl, heterocyclyl or benzyl, each substituted by s radicals selected from the group consisting of X, Y, Z and V, W is N or CY, X and Z are each independently hydrogen, halogen, $(C_1-C_6)$-alkyl, $(C_1-C_6)$-haloalkyl, $(C_2-C_6)$-alkenyl, $(C_3-C_6)$-cycloalkyl, $(C_3-C_6)$-halocycloalkyl, $OR^1$, $S(O)_nR^2$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, or heteroaryl, heterocyclyl or phenyl, each substituted by s radicals selected from the group of methyl, ethyl, methoxy, nitro, trifluoromethyl and halogen, Y is hydrogen, $(C_2-C_6)$-alkenyl, $COR^1$, $CO_2R^1$, $OCO_2R^1$, $NR^1CO_2R^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $S(O)_nR^2$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$CO_2R^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $CH=NOR^1$, $(C_1-C_6)$-alkyl-$CH=NOR^1$, $(C_1-C_6)$-alkylheteroaryl, $(C_1-C_6)$-alkylheterocyclyl, heteroaryl or heterocyclyl, where the 4 latter radicals are each substituted by s radicals selected from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, V is hydrogen, Cl, OMe, methyl or ethyl, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 21 latter radicals are substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 latter radicals are substituted by s radicals selected from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1-C_4)$-alkoxy-$(C_2-C_6)$-alkoxycarbonyl, and where heterocyclyl bears n oxo groups, $R^3$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ is $(C_1-C_6)$-alkyl, $(C_2-C_6)$-alkenyl or $(C_2-C_6)$-alkynyl, $(C_3-C_6)$-cycloalkyl or $(C_3-C_6)$-cycloalkyl-$(C_1-C_6)$-alkyl, n is 0, 1 or 2, s is 0, 1, 2 or 3, Q is a Q1, Q2, Q3 or Q4 radical

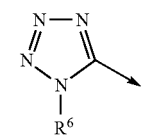
(Q1)

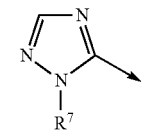
(Q2)

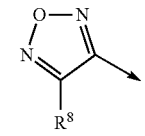
(Q3)

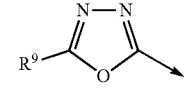
(Q4)

$R^6$ and $R^7$ are independently $(C_1-C_6)$-alkyl, halo-$(C_1-C_6)$-alkyl, or $(C_2-C_6)$-alkenyl, where these 3 aforementioned radicals are each substituted by s $(C_1-C_6)$-alkoxy radicals, $R^8$ is chlorine, methyl, methoxymethyl, amino or acetylamino, $R^9$ is methyl, ethyl, methoxymethyl or methoxyethyl.

3. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein R is methyl, or phenyl substituted in each case by s radicals selected from the group consisting of X, Y and Z, W is CY, X is F, Cl, Br, methyl, ethyl, cyclopropyl, trifluoromethyl, methoxy, methoxymethyl, methoxyethoxymethyl, SMe or $SO_2Me$, Z is hydrogen, F, Cl, Br, I, methyl, ethyl, trifluoromethyl, difluoromethyl, pentafluoroethyl, methylsulfonyl or ethylsulfonyl, Y is hydrogen, SMe, $S(O)Me$, $SO_2Me$, SEt, $S(O)Et$, $SO_2Et$, $CH_2OMe$, $CH_2OEt$, $CH_2OCH_2CF_3$, $CH_2SMe$, $CH_2S(O)Me$, $CH_2SO_2Me$, vinyl, $C(O)Me$, $C(O)Et$, C(O)cPr, CO₂Me, CHN=OMe, 4,5-dihydro-1,2-oxazol-3-yl, 5-methyl-4,5-dihydro-1,2-oxazol-3-yl, 5-methyl-4,5-dihydro-1,2-oxazol-3-yl, 5-cyanomethyl-4,5-dihydro-1,2-oxazol-3-yl, 4,5-dihydro-1,2-oxazol-5-yl, 3-methyl-4,5-dihydro-1,2-oxazol-5-yl, 1H-pyrazol-1-yl, 1H-1,2,3-triazol-1-yl, 2H-1,2,3-triazol-2-yl, 1H-1,2,4-triazol-1-yl, pyrolidin-2-on-1-yl, morpholin-3-on-4-yl, OMe, OEt, OnPr, OCH₂cPr, OCH₂CH₂F; OCH₂CH₂OMe or OCH₂CH₂CH₂OMe, V is hydrogen,
Q is a Q1, Q2, Q3 or Q4 radical

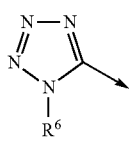 (Q1)

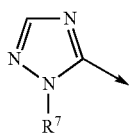 (Q2)

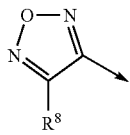 (Q3)

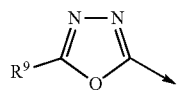 (Q4)

R⁶ is methyl or ethyl,
R⁷ is methyl,
R⁸ is chlorine or methyl,
R⁹ is methyl,
s is 0, 1, 2 or 3.

4. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein Q is Q1,

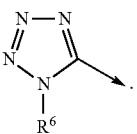 (Q1)

5. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein Q is Q2,

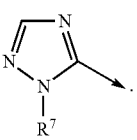 (Q2)

6. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein Q is Q3,

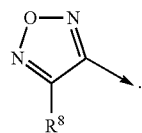 (Q3)

7. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein Q is Q4,

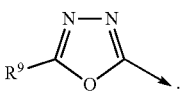 (Q4)

8. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein W is N.

9. The acylated N-(1,2,5-oxadiazol-3-yl)-, N-(1,3,4-oxadiazol-2-yl)-, N-(tetrazol-5-yl)- or N-(triazol-5-yl)arylcarboxamide of the formula (I) as claimed in claim 1, wherein
W is CY, and
Y is H.

10. The acylated N-(tetrazol-5-yl)arylcarboxamide of the formula (I) as claimed in claim 1, wherein the acylated N-(tetrazol-5-yl)arylcarboxamide is

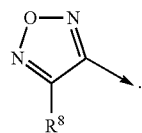

11. A herbicidal composition, comprising a herbicidally active content of at least one acylated N-(1,2,5-oxadiazol-3-yl)-, N-(1,3,4-oxadiazol-2-yl)-, N-(tetrazol-5-yl)- or N-(triazol-5-yl)-aryl carboxamide and/or salt as claimed in claim 1.

12. The herbicidal composition as claimed in claim 11 in a mixture with one or more formulation auxiliaries.

13. The herbicidal composition as claimed in claim 12, comprising a further herbicide.

14. A method of controlling one or more unwanted plants, comprising applying an effective amount of at least one acylated N-(1,2,5-oxadiazol-3-yl)-, N-(1,3,4-oxadiazol-2-yl)-, N-(tetrazol-5-yl)- or N-(triazol-5-yl)arylcarboxamide of formula (I) and/or salt as claimed in claim 1 or a herbicidal composition thereof to the plants or to a site of unwanted vegetation.

15. The method as claimed in claim 14, wherein the one or more unwanted plants are in one or more crops of useful plants.

16. The method as claimed in claim 15, wherein the useful plants are transgenic useful plants.

17. A product comprising the acylated N-(1,2,5-oxadiazol-3-yl)-, N-(1,3,4-oxadiazol-2-yl)-, N-(tetrazol-5-yl)- or N-(triazol-5-yl)arylcarboxamide of formula (I) and/or salt as claimed in claim 1 or a herbicidal composition thereof for controlling one or more unwanted plants.

* * * * *